(12) United States Patent
TenBrink

(10) Patent No.: US 6,821,970 B2
(45) Date of Patent: Nov. 23, 2004

(54) OXAZINOCARBAZOLES FOR THE TREATMENT OF CNS DISEASES

(75) Inventor: Ruth Elizabeth TenBrink, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/146,970

(22) Filed: May 16, 2002

(65) Prior Publication Data

US 2002/0169317 A1 Nov. 14, 2002

Related U.S. Application Data

(62) Division of application No. 09/620,493, filed on Jul. 20, 2000.
(60) Provisional application No. 60/146,013, filed on Jul. 28, 1999.

(51) Int. Cl.[7] .................................. A61K 31/535
(52) U.S. Cl. ........................ 514/233.2; 514/232.2
(58) Field of Search .................... 514/233.2, 232.8; 544/99

(56) References Cited

FOREIGN PATENT DOCUMENTS

| EP | 0297651 | 1/1989 | ......... C07D/403/06 |
|---|---|---|---|
| EP | 0344015 | 11/1989 | ......... C07D/471/06 |
| EP | 0377238 | 7/1990 | ......... C07D/471/16 |
| EP | 0725068 | 8/1996 | ......... C07D/471/06 |
| WO | WO 95/11245 | 4/1995 | ......... C07D/471/06 |
| WO | WO 97/45427 | 12/1997 | ......... C07D/471/04 |

OTHER PUBLICATIONS

Boess, F. G., et al., "The 5–Hydroxytryptamine6 Receptor–Selective radioligand [3H]Ro 63–0563 Labels 5–Hydroxytryptamine Receptor Binding Sites in Rat and Porcine Striatum", Mol. Phram. vol. 54, Issue 3, pp. 577–583, Sep. 1998.*
Monsama, F. J. et al., "Cloning and Expression of a Novel Serotonin Receptro with High Affinity for Tricyclic Psychotropic Drugs", Molecular Pharmacology, 43:320–327, 1993.*
Boess et al. *Mol. Pharmacol.* 1998, 54, 577–583.
Bourson et al. *Brit. J. Pharm.* 1998, 125, 1562–1566.
D. Hoyer, et al. *Pharmacol. Rev.* 1994, 46, 157–203.
Glennon, et al., *Neuroscience and Behavioral Reviews*, 1990, 14, 35.
M. D. Gershon, et al., The Peripheral Actions of 5–Hydroxytryptamine, 246 (1989).
Monsma et al. M 1. Pharmacol. 1993, 43, 320–327.
P. R. Saxena, et al., Journal of Cardiovascular Pharmacology, 15:Supplement 7 (1990).
Roth et al. *J. Pharm. Exp. Therapeut.* 1994, 268, 1403–1410.
Ruat, M. et al. Biochem. *Biophys. Res. Com.* 1993, 193, 269–276.
R. W. Fuller, Biology of Serotonergic Transmission, 221 (1982).
Sleight et al. *Brit. J. Pharmacol.* 1998, 124, 556–562.
Sleight et al. *Exp. Opin. Ther. Patents* 1998, 8, 1217–1224.
Yoshioka et al. *Life Sciences* 1998, 17/18, 1473–1477.
Abstract SU–252342–S.
Abstract SU–256776–S.
Abstract SU–255278–S.
XP–002155204 A New Photoreaction on N–Phenyl–2–Benzothiazolinone Which Produces The Previously Unreported [1,4]–Thiazino [2,3,4–jk] Carbazole System.

* cited by examiner

*Primary Examiner*—Dwayne Jones
(74) *Attorney, Agent, or Firm*—Lucy X. Yang; Mary J. Hosley

(57) ABSTRACT

The present invention provides oxazinocarbazole derivatives having a ring connecting position 8 (C-8) and position 9 (N-9), and more specifically, provides compounds of formula (I) wherein $R_1$, $R_2$, $R_3$ and $R_4$ are described herein.

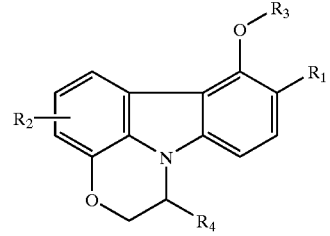

These compounds are 5-HT ligands, and are useful for treating diseases wherein modulation of 5-HT activity is desired.

29 Claims, No Drawings

OXAZINOCARBAZOLES FOR THE TREATMENT OF CNS DISEASES

This application is a divisional application or U.S. patent application Ser. No. 09/620,493, filed Jul. 20, 2002, which claims the benefit of provisional application U.S. Ser. No. 60/146,013, filed Jul. 28, 1999.

FIELD OF THE INVENTION

The present invention provides oxazinocarbazole derivatives having a ring connecting position 8 (C-8) and position 9 (N-9), and more specifically, provides compounds of formula (I) described herein below. These compounds are 5-HT ligands, and are useful for treating diseases wherein modulation of 5-HT activity is desired.

BACKGROUND OF THE INVENTION

Many diseases of the central nervous system are influenced by the adrenergic, the dopaminergic, and the serotonergic neurotransmitter systems. For example, serotonin has been implicated in a number of diseases and conditions which originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, 221 (1982); D. J. Boullin, Serotonin in Mental Abnormalities 1:316 (1978); J. Barchas, et al., Serotonin and Behavior, (1973). Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. M. D. Gershon, et al., The Peripheral Actions of 5-Hydroxytryptamine, 246 (1989); P. R. Saxena, et al., Journal of Cardiovascular Pharmacology, 15:Supplement 7 (1990).

The major classes of serotonin receptors ($5-HT_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. Recently discovered information regarding subtype identity, distribution, structure, and function suggests that it is possible to identify novel, subtype specific agents, having improved therapeutic profiles (e.g. fewer side effects).

For example, The 5-HT6 receptor was identified in 1993 (Monsma et al. Mol. Pharmacol. 1993, 43, 320–327 and Ruat, M. et al. Biochem. Biophys. Res. Com. 1993, 193, 269–276). Several antidepressants and atypical antipsychotics bind to the 5-HT6 receptor with high affinity and this binding may be a factor in their profile of activities (Roth et al. J. Pharm. Exp. Therapeut. 1994, 268, 1403–1410; Sleight et al. Exp. Opin. Ther. Patents 1998, 8, 1217–1224; Bourson et al. Brit. J. Pharm. 1998, 125, 1562–1566; Boess et al. Mol. Pharmacol. 1998, 54, 577–583; Sleight et al. Brit. J. Pharmacol. 1998, 124, 556–562). In addition, the 5-HT6 receptor has been linked to generalized stress and anxiety states (Yoshioka et al. Life Sciences 1998, 17/18, 1473–1477). Together these studies and observations suggest that compounds that antagonize the $5-HT_6$ receptor will be useful in treating disorders of the central nervous system.

Compounds of the present invention are 5-HT ligands (e.g. receptor-specific agonists or antagonists). Thus they are useful for treating diseases wherein modulation of 5-HT activity is desired. Specifically, the compounds of this invention are useful in the treatment of psychosis, paraphrenia, psychotic depression, mania, schizophrenia, schizophreniform disorders, anxiety, migraine headache, drug addiction, convulsive disorders, personality disorders, post-traumatic stress syndrome, alcoholism, panic attacks, obsessive-compulsive disorders, and sleep disorders. The compounds of this invention are also useful to treat psychotic, affective, vegetative, and psychomotor symptoms of schizophrenia and the extrapyramidal motor side effects of other antipsychotic drugs. This last action will allow higher doses of antipsychotics to be used and thus greater antipsychotic efficacy to be obtained as a result of a reduction in side effects. The compounds of this invention are also useful in the modulation of eating behavior and thus are useful in treating excess weight and associated morbidity and mortality.

INFORMATION DISCLOSURE

International Publication No. WO97/45427 discloses pyridocarbazole derivatives having a highly selective cyclic GMP-phosphodiesterease inhibitory effect.

International Publication No. WO95/11245 discloses tetracyclic indole derivatives which have a selective antagonism against intestinal 5-HT3 receptors and are useful for preventing or treating digestive tract disorders such as irritable bowel syndrome and diarrhea.

Abstracts of SU-256776-S, SU-252342-S and SU-255278-S disclose 1,2-dihydropyrazino carbazoles useful as intermediates in the synthesis of biologically active compounds.

European Patent Application EP 377238 discloses annelated indolo [3,2-c] lactam derivatives having an antagonistic activity on 5-HT receptors. The compounds can be used for the treatment gastrointestinal system disorders, central nervous system disorders, cardiovascular disorders, respiratory system disorders, and for alleviating or preventing withdrawal symptoms which are induced by abuse of drugs.

European Patent Application EP 344015 discloses tetracyclic ketones useful in the treatment of psychotic disorders, anxiety, nausea, and vomiting in which a cyclohexanone ring system is fused to an indole system.

European Patent Application EP 297651 discloses tetracyclic ketones useful as antagonists of serotonin receptors in which a cyclohexanone ring system is attached to an indole system.

SUMMARY OF THE INVENTION

The present invention provides a compound of formula I

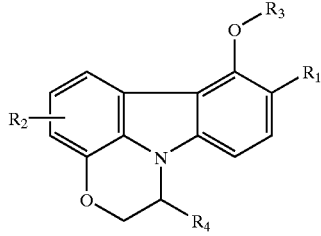

or a pharmaceutically acceptable salt thereof wherein $R_1$ is
(a) H,
(b) halo, or
(c) $C_{1-6}$ alkyl;

$R_2$ is
(a) H,
(b) halo,
(c) —OH,
(d) —CN,
(e) —CF$_3$,
(f) —O(C$_{1-6}$)alkyl,
(g) $C_{1-6}$ alkyl,
(h) $C_{3-6}$ cycloalkyl,
(i) —NR$_5$R$_6$,
(j) —CONR$_5$R$_6$,
(k) —SO$_2$NR$_5$R$_6$,
(l) —COOR$_7$, or
(m) phenyl, optionally substituted with halo, OH, O(C$_{1-4}$) alkyl, or $C_{1-6}$ alkyl;

$R_3$ is
(a) —(CH$_2$)$_m$—NR$_8$R$_9$ wherein the —(CH$_2$)$_m$—chain may be substituted with one or two $C_{1-6}$ alkyl or $C_{3-6}$ cycloalkyl;

$R_4$ is
(a) aryl, or
(b) heteroaryl;

aryl is phenyl or naphthyl, optionally substituted with one or more $R_{10}$;

hetetoaryl is a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein X is absent, H or $C_{1-4}$ alkyl; wherein carbon atoms of heteroaryl may be substituted with one or more $R_{10}$;

$R_5$ and $R_6$ is independently
(a) H,
(b) $C_{1-6}$ alkyl, or
(c) $C_{3-6}$ cycloalkyl;

$R_7$ is
(a) $C_{1-6}$ alkyl, or
(b) ($C_{1-3}$ alkyl)-phenyl wherein phenyl may be substituted with $R_{10}$;

$R_8$ and $R_9$ is independently
(a) H,
(b) $C_{1-6}$ alkyl,
(c) $C_{3-6}$ cycloalkyl,
(a) $C_{2-4}$ alkyl substituted with —OH, —O(C$_{1-4}$ alkyl), —O(C$_{1-4}$ alkyl)—NR$_{11}$R$_{12}$, or —CO$_2$R$_5$,
(e) —CHO, with the proviso that only one of the $R_8$ and $R_9$ is CHO, the other one is hydrogen,
(f) —(CH$_2$)$_m$—phenyl wherein the phenyl may be substituted with halo, or
(g) $R_8$ and $R_9$ taken together with the nitrogen to which they are attached form a five-, six-, or seven-membered heterocyclic ring wherein the heterocyclic ring optionally has one to two additional heteroatoms selected from the group consisting of oxygen, sulfur and N(Y) and wherein the carbon atoms of the heterocyclic ring is optionally substituted with one or two $R_{13}$;

Y is absent or $R_{14}$;

$R_{10}$ is
(a) halo,
(b) —OH,
(c) —CN,
(d) —CF$_3$,
(e) —O(C$_{1-6}$)alkyl,
(f) $C_{1-6}$ alkyl,
(g) $C_{3-6}$ cycloalkyl,
(h) —NR$_5$R$_6$,
(i) —CONR$_5$R$_6$,
(j) —SO$_2$NR$_5$R$_6$,
(k) —COOR$_7$, or
(l) phenyl, optionally substituted with halo, OH, O(C$_{1-4}$) alkyl, or $C_{1-6}$ alkyl;

$R_{11}$ and $R_{12}$ is independently,
(a) H, or
(b) $C_{1-4}$ alkyl;

$R_{13}$ is
(a) $C_{1-6}$ alkyl,
(b) $C_{3-6}$ cycloalkyl,
(c) $C_{2-4}$ alkyl substituted with —OH, —O(C$_{1-4}$ alkyl), —O(C$_{1-4}$ alkyl)—NR$_{10}$R$_{11}$, or —CO$_2$R$_5$,
(d) —OH, or
(e) oxo (=O);

$R_{14}$ is
(a) H,
(b) $C_{1-6}$ alkyl,
(c) $C_{3-6}$ cycloalkyl,
(d) $C_{2-4}$ alkyl substituted with —OH, —O(C$_{1-4}$ alkyl), —O(C$_{1-4}$ alkyl)—NR$_{10}$R$_{11}$, or —CO$_2$R$_5$,
(e) —COOR$_7$,
(f) —OH, or
(g) oxo (=O);

and m is 2, 3 or 4.

The present invention further provides a pharmaceutical composition comprising a compound of formula I, or a pharmaceutically acceptable salt thereof, and a pharmaceutically acceptable carrier. In preferred embodiments, the composition preferably comprises a therapeutically effective amount of a compound of formula I or a pharmaceutically acceptable salt thereof.

The present invention further provides a method for treating a disease or condition in a mammal wherein a 5-HT receptor is implicated and modulation of a 5-HT function is desired comprising administering to the mammal a therapeutically effective amount of a compound of formula I, or a pharmaceutically acceptable salt thereof.

The present invention further provides a method for treating a disease or condition in a mammal wherein a 5-HT$_6$ receptor is implicated and modulation of a 5-HT$_6$ function is desired comprising administering to the mammal a therapeutically effective amount of a compound of formula III, or a pharmaceutically acceptable salt thereof;

The present invention further provides a method for treating or preventing diseases or disorders of the central nervous system comprising administering a therapeutically effective amount of a compound of formula I, or a pharmaceutically acceptable salt thereof to the mammal. Diseases or disorders for which a compound of formula I may have activity include, but are not limited to the following: obesity, depression, schizophrenia, schizophreniform disorder, schizoaffective disorder, delusional disorder, a stress related disease (e.g. general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific developmental disorder, agitation disorder, selective serotonin reuptake inhibition (SSRI) "poop out" syndrome or a Tic disorder (e.g., Tourette's syndrome).

The present invention further provides a method for treating anxiety, depression or stress related disorders comprising administering a therapeutically effective amount of a compound of formula I, or a pharmaceutically acceptable salt thereof to the mammal.

The present invention further provides the use of a compound of formula I or a pharmaceutically acceptable salt thereof to prepare a medicament for treating or preventing diseases or disorders of the central nervous system.

The present invention further provides a method for modulating 5-HT receptor function, comprising contacting (in vitro or in vivo) the receptor with an effective inhibitory amount of a compound of formula I or a pharmaceutically acceptable salt thereof.

The invention also provides novel intermediates and processes for preparing compounds of formula I.

DETAILED DESCRIPTION OF THE INVENTION

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

Specific and preferred values listed below for radicals, substituents, and ranges, are for illustration only; they do not exclude other defined values or other values within defined ranges for the radicals and substituents.

The following definitions are used, unless otherwise described.

Halo is fluoro, chloro, bromo, or iodo.

Alkyl denotes both straight and branched groups; but reference to an individual radical such as "propyl" embraces only the straight chain radical, a branched chain isomer such as "isopropyl" being specifically referred to. Specifically, $C_{1-7}$ alkyl can be methyl, ethyl, propyl, isopropyl, butyl, iso-butyl, sec-butyl, pentyl, 3-pentyl, or hexyl.

$C_{3-6}$ cycloalkyl denotes a cycloalkyl having three to six carbon atoms. Specifically, $C_{3-6}$ cycloalkyl can be cyclopropyl, cyclobutyl, cyclopentyl, or cyclohexyl.

Aryl denotes a phenyl or a naphthyl radical. Optionally, aryl is substituted with one or more halo, OH, CN, $CF_3$, $O(C_{1-6})$alkyl, $C_{-1-6}$ alkyl, $C_{3-6}$ cycloalkyl, $NR_5R_6$, $CONR_5R_6$, $SO_2NR_5R_6$, $COOR_7$, or phenyl which in turn may be substituted with halo, OH, $O(C_{1-4})$ alkyl, or $C_{1-6}$ alkyl.

Heteroaryl denotes a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein X is absent, H or $C_{1-4}$ alkyl; wherein carbon atoms of heteroaryl may be substituted with one or more halo, OH, CN, $CF_3$, $O(C_{1-6})$alkyl, $C_{1-6}$ alkyl, $C_{3-6}$ cycloalkyl, $NR_5R_6$, $CONR_5R_6$, $SO_2NR_5R_6$, $COOR_7$, or phenyl which in turn may be substituted with halo, OH, $O(C_{1-4})$ alkyl, or $C_{1-6}$ alkyl. Specifically, heteroaryl can be pyridyl, thiophene, benzothiophene, benzofuran, benzimidazole, imidazole or thiazole.

Pharmaceutically acceptable salts denotes acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, methanesulfonic acid salt and etc. Specifically, pharmaceutically acceptable salts can be maleate, methanesulfonic acid salt and etc.

Mammal denotes human and animals.

A specific value for $R_1$ includes H, halo, or $C_{1-6}$ alkyl.

A specific value for $R_1$ includes H or chloro.

A specific value for $R_2$ includes H, halo, —OH, —CN, —$CF_3$, —$O(C_{1-6})$alkyl, $C_{1-6}$ alkyl, $C_{3-6}$ cycloalkyl, —$NR_5R_6$, —$CONR_5R_6$, —$SO_2NR_5R_6$, —$COOR_7$, or phenyl which may be substituted with halo, —OH, —$O(C_{1-4})$ alkyl, or $C_{1-6}$ alkyl; wherein $R_5$ and $R_6$ is H, $C_{1-6}$ alkyl, or $C_{3-6}$ cycloalkyl; wherein $R_7$ is $C_{1-6}$ alkyl, or ($C_{1-3}$ alkyl)-phenyl wherein phenyl may be substituted with $R_2$.

A specific value for $R_2$ includes H, halo, or $C_{1-6}$ alkyl.

A specific value for $R_2$ includes H, chloro, fluoro, or methyl.

A specific value for $R_2$ includes H, or methyl.

A specific value for $R_3$ includes —$(CH_2)_m$—$NR_8R_9$, wherein the —$(CH_2)_m$—chain may be substituted with one or more $C_{1-6}$ alkyl or $C_{3-6}$ cycloalkyl; wherein $R_8$ and $R_9$ is independently H, $C_{1-6}$ alkyl, $C_{3-6}$ cycloalkyl, $C_{2-4}$ alkyl substituted with OH, —$O(C_{1-4}$ alkyl), —$O(C_{1-4}$ alkyl)—$NR_{10}R_{11}$ or —$CO_2R_5$, —CHO (with the proviso that only one of the $R_8$ and $R_9$ is —CHO, the other one is hydrogen), —$(CH_2)_m$—phenyl wherein the phenyl may be substituted with halo, or $R_8$ and $R_9$ taken together with the nitrogen to which they are attached form a five-, six-, or seven-membered heterocyclic ring wherein the heterocyclic ring optionally has one to two additional heteroatoms selected from the group consisting of oxygen, sulfur and N(Y) and wherein the carbon atoms of the heterocyclic ring is optionally substituted with one or two $R_{13}$; wherein Y is absent or $R_{14}$; wherein $R_{10}$ and $R_{11}$ is independently H, or $C_{1-4}$ alkyl; $R_{13}$ is $C_{1-6}$ alkyl, $C_{3-6}$ cycloalkyl, $C_{2-4}$ alkyl substituted with —OH, —O($C_{1-4}$ alkyl), —O($C_{1-4}$ alkyl)—$NR_{10}R_{11}$ or —$CO_2R_5$, —OH, or oxo (=O); $R_{14}$ is H, $C_{1-6}$ alkyl, $C_{3-6}$ cycloalkyl, $C_{2-4}$ alkyl substituted with —OH, —O($C_{1-4}$ alkyl), —O($C_{1-4}$ alkyl)—$NR_{10}R_{11}$ or —$CO_2R_5$, —$COOR_7$, —OH, or oxo (=O).

A specific value for $R_3$ includes —$(CH_2)_2$—$NR_8R_9$, wherein $R_8$ and $R_9$ is independently H, $C_{1-4}$ alkyl, $C_{2-4}$ alkyl substituted with —OH, —CHO (with the proviso that only one of the $R_8$ and $R_9$ is —CHO, the other one is hydrogen), or $R_8$ and $R_9$ taken together with the nitrogen to which they are attached form piperidinyl, pyrrolidinyl, morpholinyl, thiomorpholinyl, piperazinyl or azetidinyl, wherein one of the nitrogen atoms on the piperazinyl ring is substituted with H, $C_{1-4}$ alkyl, or —$CO_2(C_{1-4}$ alkyl).

A specific value for $R_3$ includes —$(CH_2)_2$—$NR_8R_9$, wherein $R_8$ and $R_9$ is independently H, methyl, ethyl, ethanol, isopropyl, or $R_8$ and $R_9$ taken together with the nitrogen to which they are attached form 1-piperazinyl, 4-methyl-1-piperazinyl, 4-tert-butyl-1-piperazinecarboxylate, 4-morpholinyl, 1-piperidinyl, 1-pyrrolidine or —CHO with the proviso that only one of the $R_8$ and $R_9$ is —CHO, the other one is hydrogen.

A specific value for $R_4$ includes aryl, wherein aryl is defined as herein above.

A specific value for $R_4$ includes substituted or unsubstituted phenyl.

A specific value for $R_4$ includes heteroaryl.

A specific value for $R_4$ includes pyridyl, pyrazinyl, pyridazinyl, pyrimidinyl, triazinyl, quinolinyl, thiophenyl, furanyl, or pyrrolyl, A specific value for $R_4$ is phenyl.

Examples of the present invention includes:

a) (S)-(+)-[(1-phenyl-1,2-dihydro[1,4]oxazino[2,3,4-jk]carbazol-7-yl)oxy]ethanamine, b) (R)-(−)-[(1-phenyl-1,2-dihydro[1,4]oxazino[2,3,4-jk]carbazol-7-yl)oxy]ethanamine, c) N,N-diethyl-2-[(1-phenyl-1,2-dihydro[1,4]oxazino[2,3,4-jk]carbazol-7-yl)oxy]-1-ethanamine, d) [(1-phenyl-1,2-dihydro[1,4]oxazino[2,3,4-jk]carbazol-7-yl)oxy]ethanamine, e) N-isopropyl-N-{2-[(1-phenyl-1,2-dihydro[1,4]oxazino[2,3,4-jk]carbazol-7-yl)oxy]ethyl}amine, f) N-ethyl-2-[(1-phenyl-1,2-dihydro[1,4]oxazino[2,3,4-jk]carbazol-7-yl)oxy]-1-ethanamine, g) 2-[(1-phenyl-1,2-dihydro[1,4]oxazino[2,3,4-jk]carbazol-7-yl)oxy]ethylformamide, h) N-methyl-2-[(1-phenyl-1,2-dihydro[1,4]oxazino[2,3,4-jk]carbazol-7-yl)oxy]-1-ethanamine, i) 2-[(8-chloro-1-phenyl-1,2-dihydro[1,4]oxazino[2,3,4-jk]carbazol-7-yl)oxy]-1-ethanamine, j) 2-[(5-methyl-1-phenyl-1,2-dihydro[1,4]oxazino[2,3,4-jk]carbazol-7-yl)oxy]-1-ethanamine, k) N-ethyl-2-[(5-methyl-1-phenyl-1,2-dihydro[1,4]oxazino[2,3,4-jk]carbazol-7-yl)oxy]-1-ethanamine, l) tert-butyl 4-{2-[(1-phenyl-1,2-dihydro[1,4]oxazino[2,3,4-jk]carbazol-7-yl)oxy]ethyl}-1-piperazinecarboxylate, m) 1-phenyl-1,2-dihydro[1,4]oxazino[2,3,4-jk]carbazol-7-yl 2-(1-piperazinyl)ethyl ether, n) 2-(4-methyl-1-piperazinyl)ethyl 1-phenyl-1,2-ihydro[1,4]oxazino [2,3,4-jk]carbazol-7-yl ether, o) 2-(4-morpholinyl)ethyl 1-phenyl-1,2-dihydro[1,4]oxazino[2,3,4-jk]carbazol-7-yl ether, p) 1-phenyl-1,2-dihydro[1,4]oxazino[2,3,4-jk]carbazol-7-yl 2-(1-piperidinyl)ethyl ether, q) 2-({2-[(1-phenyl-1,2-dihydro[1,4]oxazino[2,3,4-jk]carbazol-7-yl)oxy]ethyl}amino)-1-ethanol, r) N,N-dimethyl-2-[(1-phenyl-1,2-dihydro[1,4]oxazino[2,3,4-jk]carbazol-7-yl)oxy]-1-ethanamine, s) 2-[(5-Methyl-1-phenyl-1,2-dihydro[1,4]oxazino[2,3,4-jk]carbazol-7-yl)oxy]-1-ethanamine, t) N,N-Diethyl-N-{4-[(1-phenyl-1,2-dihydro[1,4]oxazino[2,3,4-jk]carbazol-7-yl)oxy]butyl}-amine, u) N,N-Diethyl-N-{3-[(1-phenyl-1,2-dihydro[1,4]oxazino[2,3,4-jk]carbazol-7-yl)oxy]propyl}amine, v) [(2-{[(1R)-1-Phenyl-1,2-dihydro[1,4]oxazino[2,3,4-jk]carbazol-7-yl)oxy]}ethyl)amino]ethanol, or pharmaceutically acceptable salt thereof.

It will be appreciated by those skilled in the art that compounds of the invention contain a chiral center, therefore, they may be isolated in optically active or racemic forms. Some compounds may exhibit polymorphism. It is to be understood that the present invention encompasses any racemic, optically active, polymorphic, tautomeric, or stereoisomeric form, or mixture thereof, of a compound of the invention, which possesses the useful properties described herein. It is well known in the art to prepare optically active forms (for example, by resolution of the racemic form by recrystallization techniques, by synthesis from optically-active starting materials, by chiral synthesis, or by chromatographic separation (using a chiral stationary phase, for example) and to determine 5-$HT_6$ activity using the standard tests described herein, or using other similar tests which are well known in the art.

The following Schemes describe the preparation of compounds of the present invention. All of the starting materials are commercially available or prepared by procedures described in these schemes or by procedures that would be well known to one of ordinary skill in organic chemistry. The variables used in the Schemes are as defined above or as in the claims.

Chart A discloses several methods of preparing benzoxazine 6. Nitrophenol 1 can be alkylated with an alpha halo ketone 2 using a base such as sodium carbonate, potassium carbonate, cesium carbonate, sodium bicarbonate, sodium hydride, and sodium hydroxide in solvents such as DMF, THF, acetone, dichloromethane, or acetonitrile to give nitro ether 3. Reduction of the nitro group of 3 with reducing agents such as hydrogen and palladium on carbon or tin (II) chloride or other reducing agents (see, for example, March, J. *Advanced Organic Chemistry*, 3rd ed., John Wiley and Sons: New York: 1985) gives oxazine imine 5, which upon further treatment with reducing agents such as hydrogen and palladium on carbon or sodium borohydride in solvents such as ethanol, methanol, and water gives benzoxazine 6. Alternatively, oxazine imine 5 is prepared from amino phenol 4 and alpha halo ketone 2 in the presence of a phase transfer catalyst and dichloromethane and aqueous potassium carbonate (see Sabitha and Rao, *Synthetic Communications* 1987, 17, 341).

Benzoxazine 6 contains a chiral center. The individual enantiomers may be obtained by several methods. One method is chromatography on a chiral stationary phase to give the individual enantiomers (see *Chiral Separations by Liquid Chromatography*, Ahuja, S., ed., American Chemical Society, Washington, D.C.: 1991, and *Chiral Separations by HPLC: Application to Pharmaceutical Compounds*, Krstulovic, A. M., ed., Ellis Norwood Limited: Chicester: 1989). Another method of obtaining the enantiomers is through reduction of oxazine imine 5 with chiral reducing agents used either stoichiometrically or catalytically. One method of using a stoichiometric amount of a chiral reducing agent is to prepare the reducing agent from sodium borohydride and an N-protected L- or D-amino acid (see Atarashi, et al. *J. Heterocyclic Chem.* 1991, 28, 329 and Yamada et al. *J. Chem. Soc. Perkin Trans. I* 1983, 265). For example, the use of CBZ-L-proline in the reagent prepared according to these references gives (+)-benzoxazine 6 as the major enantiomer. Another method of preparing benzoxazine 6 in chiral form is through the use of a chiral catalyst in the presence of a reducing agent as set forth by Noyori et al. (*J. Am. Chem. Soc.* 1996, 118, 4916), Buchwald et al. (*J. Am. Chem. Soc.* 1996, 118, 6784 and *Ang. Chem. Int. Ed. Engl.* 1998, 37, 1103) and others. Structures 6, 7, 8 and 9 are either racemics or individual enantiomers in Chart A and the subsequent reactions schemes. For illustration, only the racemic form is depicted.

Next, benzoxazine 6 is stirred in an acidic solvent such as TFA, acetic acid, or aq. sulfuric acid. A nitrite such as sodium nitrite, isoamylnitrite, t-butylnitrite, or n-butylnitrite is added to give N-nitrosoamine 7. N-nitrosoamine 7 is reduced with lithium aluminum hydride in ether or THF to give the hydrazine 8, which can be reacted with cyclohexane-1,3-dione under Fischer indole conditions to give the oxotetrahydrooxazinocarbazole 9 (see Sundberg, R. J.; *Indoles*, Academic Press: London; 1996, and in Hughes, D. L. Progress in the Fischer Indole Reaction: A Review. *Org. Prep. Proceed. Int.* 1993, 25, 609–632). When 9 is racemic, it is conveniently separated into its enantiomers by chromatography on a column packed with a chiral stationary phase and using an eluant such as isopranol/hexane. (see *Chiral Separations by Liquid Chromatography*, Ahuja, S., ed., American Chemical Society, Washington, D.C.: 1991, and *Chiral Separations by HPLC: Application to Pharmaceutical Compounds*, Krstulovic, A. M., ed., Ellis Norwood Limited: Chicester: 1989).

Charts B, C, and D depict only the racemate, but the methods given apply as well to the individual enantiomers.

In Chart B, phenol 12 can be prepared from structure 9 in a single step using Raney nickel in solvents such as cumene, mesitylene, 1,2,3-trimethylbenzene, 1,2,4-trimethylbenzene, decalin, and diphenyl ether at temperatures between 130–270° C. to give phenol 12 directly. A second method is heating 9 in 2-(ethoxyethoxy)ethanol at about 160–210° C. in the presence of Pd on carbon or Darco, or a mixture thereof (see European patent EP839806). Alternatively, structure 9 is first treated with a copper (II) halide, preferably $CuCl_2$ or $CuBr_2$, in either their anhydrous or hydrated form, in solvents such as ethylene glycol, ethylene glycol/doixane, ethylene glycol/THF, DMF, acetonitrile, ethyl acetate, chloroform, acetic acid, or acetic acid/water at temperatures between 40° C. and 120° C. to give halo ketones 10 and 11. For a reference to this reaction, see Matsumoto, M.; Ishida, Y.; Watanabe, N. *Heterocycles* 1985, 23, 165–170. A mixture of mono and dihalo ketones 10 and 11, respectively, are usually obtained with halogenating reagents such as the copper halides. Halo ketones 10 and 11 may be separated by chromatography on silica gel and carried on to 12 and 13, or they may be carried forward as a mixture in the next step and separated in at that time. The halo ketones 10 and 11 (separately or together) are then treated with lithium chloride or lithium bromide (anhydrous LiCl or LiBr are preferred, but hydrated forms also may be used) in the presence of lithium carbonate, or with potassium carbonate with or without added lithum halide salts in a solvent such as DMF at 100–270° C. to give phenols 12 and 13. Alternatively, 9 may be alkylated using an alkylating agent such as methyl iodide in the presence of a base such as NaH, KO-t-Bu, or LDA in solvents such as THF at temperature ranging from about −78° C. to room temperature to give 10, which may be converted to 12 using the methods described for the direct conversion of 9 to 12.

Phenols 12 and 13 may be alkylated with various alkylating agents to give oxazino amines 16, 17, 19, 20, and 24 directly or after several steps. Which method is used will depend on the type of amine which is desired and on the availability of alkylating agents and amines.

As shown in Chart B phenols 12 and 13 are alkylated with dialkylaminoalkylchlorides in the presence of bases such as sodium hydride, potassium carbonate, cesium carbonate, or sodium carbonate in solvents such as DMF, acetonitrile, or acetone at room temperature to 120° C. using methods well-known to those versed in the art to give oxazine amines 16 and 17. Alternatively, phenols 12 and 13 are alkylated with chloro or bromoalkylnitrile in the presence of bases such as sodium hydride, potassium carbonate, cesium carbonate, or sodium carbonate in solvents such as DMF, acetonitrile, or acetone to give nitriles 14 and 15. Reduction of the nitrile with borane in THF or borane-methyl sulfide complex in THF at room temperature to 80° C. gives oxazino amines 16 and 17.

Chart C discloses further functionalization of oxazino amine 16 (or 17) by several methods. One method is acylation with acylation agents such as ethyl formate, acetic anhydride, and the like to give acyl oxazinocarbazole 18. The carbonyl group of acyl oxazinocarbazole 18 is reduced to an alkyl group using reagents such as borane in THF or borane-methyl sulfide complex in THF at room temperature to 80° C. to give alkylamino oxazinocarbazole 19. Another method is reduction using lithium aluminum hydride in ethereal solvents to effect the reduction of 18 to alkylamino oxazinocarbazole 19. Another method for the preparation of oxazinocarbazole 19 is reductive amination of 16 with an equivalent amount of an aldehyde or ketone in the presence of reducing agents such as sodium cyanoborohydride or sodium triacetoxyborohydride in solvents such as dichloromethane, dichloroethane, and THF at 0 to 80° C., or Pd/C under a hydrogen atmosphere in solvents such as methanol, ethanol, or ethyl acetate, to give 19. A third method is alkylation of oxazino amine 16 with alkyl halides or mesylates or tosylates in the presence of base in solvents such as THF, acetonitrile, dichloromethane, DMF and the like using methods well known to those versed in the art, to give 19. In Chart C, Q is hydrogen, alkyl, or aryl. Z is hydrogen or alkyl. X is halo or sulfonate.

When dialkylarmino oxazinocarbazole 20 is desired, a second equivalent of the same or a different aldehyde or alkylating agent is added to alkylamino oxazinocarbazole 19 using the conditions described above. Alternatively, excess alkylating agent or aldehyde or ketone may be used starting with 16 to give 20 directly.

Chart D describes two other methods of preparing mono or dialkylamino oxazines 24. Phenol 12 (or 13) is alkylated with halo alkyl halides in the presence of bases such as potassium carbonate, cesium carbonate, and NaH in solvents such as DMF, acetonitrile, THF, dichloromethane, and acetone at room temperature to 120° C. to give oxazine halide 21. Halo oxazine 21 is then treated with an amine in the presence of a base such as potassium carbonate, TEA, DIEA in solvents such as DMF, acetonitrile, THF, dichloromethane, or acetone at room temperature to 120° C. to give amino oxazine 24. Another route to amino oxazine 24 is by way of alkylation of phenol 12 with hydroxyalkyl halide to give oxazine alcohol 22. The alcohol group is converted to a leaving group with methane sulfonyl halide or toluene sulfonyl halide to give oxazine sulfonate 23. The O-sulfonate group is then displaced by amines to give amino oxazine 24.

Pharmaceutically acceptable salts may be obtained using standard procedures well known in the art, for example by mixing a compound of the present invention with a suitable acid.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Pubi. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 30 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

Generally, compounds of the invention are 5-HT ligands. The ability of a compound of the invention to bind or act at a 5-HT receptor, or to bind or act selectively at a specific 5-HT receptor subtype can be determined using in vitro and in vivo assays that are known in the art. As used herein, the term "bind selectively" means a compound binds at least 2 times, preferably at least 10 times, and more preferably at least 50 times more readily to a given 5-HT subtype than to one or more other subtypes. Preferred compounds of the invention bind selectively to one or more 5-HT receptor subtypes.

The ability of a compound of the invention to act as a 5-HT receptor agonist or antagonist can also be determined using in vitro and in vivo assays that are known in the art. The invention provides compounds of formula I that act as either agonists or as antagonists of one or more 5-HT receptor subtypes.

5-HT$_6$ Receport Binding Assay
Growth of Cells and Membrane Preparation

Hela cells containing the cloned human 5-HT$_6$ receptor were acquired from Dr. David R. Sibley's laboratory in National Institute of Health (see Sibley, D. R., *J. Neurochemistry*, 66, 47–56, 1996). Cells were grown in high glucose Dulbecco's modified Eagle's medium, supplemented with L-glutamine, 0.5% sodium pyruvate, 0.3% penicillin-streptomycin, 0.025% G-418 and 5% Gibco fetal bovine serum and then were harvested, when confluent, in cold phosphate buffered saline.

Harvested intact cells were washed once in cold phosphate-buffered saline. The cells were pelleted and resuspended in 100 ml of cold 50 mM Tris, 5 mM EDTA and 5 mM EGTA, pH 7.4. Homogenization was with a Vir Tishear generator, 4 cycles for 30 seconds each at setting 50. The homogenized cells were centrifuged at 700 RPM (1000×g) for 10 minutes and the supernatant was removed. The pellet was resuspended in 100 ml of the above buffer and rehomogenized for 2 cycles. The rehomogenized cells were then centrifuged at 700 RPM (1000×g) for 10 minutes and the supernatant was removed. The combined supernatant (200 ml) was centrifuged at 23,000 RPM (80,000×g) for 1 hour in a Beckman Rotor (42.1 Ti). The membrane pellet was resupended in 50–8-ml of assay buffer containing HEPES 20 mM, MgCl2 10 mM, NaCl 150 mM, EDTA 1 mM, pH 7.4 and stored frozen in aliqouts at −70° C.

5-HT$_6$ Receptor Binding Assay

The radioligand binding assay used [$^3$H]-lysergic acid diethylamide (LSD). The assay was carried out in Wallac 96-well sample plates by the addition of 11 µl of the test sample at the appropriate dilution (the assay employed 11 serial concentrations of samples run in duplicate), 11 µl of radioligand, and 178 µl of a washed mixture of WGA-coated SPA beads and membranes in binding buffer. The plates were shaken for about 5 minutes and then incubated at room temperature for 1 hour. The plates were then loaded into counting cassettes and counted in a Wallac MicroBeta Trilux scintillation counter.

Binding Constant (Ki) Determination

Eleven serial dilutions of test compounds were distributed to assay plates using the PE/Cetus Pro/Pette pipetter. These dilutions were, followed by radioligand and the bead-membrane mixture prepared as described above. The specifically bound cpm obtained were fit to a one-site binding model using GraphPad Prism ver. 2.0. Estimated IC$_{50}$ values were converted to Ki values using the Cheng-Prusoff equation (Cheng, Y. C. et al., *Biochem. Pharmacol.*, 22, 3099–108, 1973). The Ki values obtained from the assay are shown in Table 1.

TABLE 1

5-HT$_6$ receptor Binding Assay Data

| EXAMPLE NO. | Ki (nM) |
|---|---|
| 1 | 76 |
| 2 | 1.8 |
| 3 | 7.6 |
| 4 | 1.7 |
| 5 | 7.8 |
| 6 | 2.7 |
| 7 | 39 |
| 8 | 2 |
| 9 | 5.8 |
| 11 | 5.3 |
| 12 | 35 |
| 13 | 57 |
| 14 | 6.9 |
| 15 | 97 |
| 16 | 5 |
| 17 | 1.1 |
| 18 | 3.3 |
| 19 | 8 |
| 20 | 28 |
| 21 | 19 |
| 22 | 3 |

The compounds and their preparations of the present invention will be better understood in connection with the following examples, which are intended as an illustration of and not a limitation upon the scope of the invention.

EXAMPLES OF PREFERRED EMBODIMENTS

Preparation 1 3-Phenyl-2H-1,4-benzoxazine

To potassium carbonate (72 g, 521 mmol) in water (360 mL) and CH$_2$Cl$_2$ (400 mL) is added 2-aminophenol (10.05 g, 92.1 mmol) and tetra-n-butyl ammonium hydrogensulfate (0.156 g, 0.46 mmol). With vigorous stirring a solution of 2-bromoacetophenone (18.33 g, 92.1 mmol) in CH$_2$Cl$_2$ (150 mL) is added dropwise over a period of 45 min. The mixture is allowed to stir overnight. The layers are separated and the organic layer is washed 3 times with water (300 mL), dried over magnesium sulfate and concentrated to dryness. The resulting solid is recrystallized from absolute ethanol (50 mL) to yield 11.78 g (61%) of 3-phenyl-2H-1,4-benzoxazine; mp 108–111° C.

IR (drift) 1613, 1479, 1445, 1389, 1320, 1274, 1216, 1111, 1078, 1064, 937, 885, 754, 736, 689 cm$^{-1}$; $^1$H NMR (CDCl$_3$) δ 5.08, 6.91, 7.01, 7.13, 7.47, 7.93. Anal. Calcd for C$_{14}$H$_{11}$NO: C, 80.36; H, 5.30; N, 6.69. Found: C, 80.15; H, 5.34; N, 6.63.

Preparation 2a 3-Phenyl-3,4-dihydro-2H-1,4-benzoxazine

To a slurry of 3-phenyl-2H-1,4-benzoxazine (17 g, 81.2 mmol) in 100 mL absolute ethanol is added sodium borohydride (6.07 g, 162.4 mmol) and water (25 mL). The mixture is heated at 90° C. for 2 h. The mixture is cooled and concentrated, then partitioned between CH$_2$Cl$_2$ and water. The organic layer is washed twice with water (200 mL), dried over magnesium sulfate and concentrated. The resulting oil is dried under high vacuum to give 15.95 g (93%) of 3-phenyl-3,4-dihydro-2H-1,4-benzoxazine.

IR (liq.) 1609, 1591, 1501, 1480, 1453, 1428, 1350, 1313, 1280, 1210, 1128, 1056, 1039, 744, 700 cm$^{-1}$; $^1$H NMR (CDCl$_3$) δ 3.99, 4.28, 4.50, 6., 6.79, 6.85, 7.41. Anal. Calcd for C$_{14}$H$_{13}$NO: C, 79.59; H, 6.20; N, 6.63. Found: C, 79.22; H, 6.27; N, 6.38.

Preparation 2b (3R)-3-Phenyl-3,4-dihydro-2H-1,4-benzoxazine

The product of PREPARATION 2b (5.01 g, 23.7 mmol) is dissolved in 25 ml of dichloromethane at ambient temperature and treated with N-methylmorpholine (2.3 g, 22.5 mmol). The resulting solution is stirred and cooled to −20° C. A solution of (S)-naproxen chloride (4.43 g, 17.8 mmol) in 25 ml of dichloromethane is added dropwise over 15 minutes, maintaining the reaction temperature below −17° C. The reaction mixture is stirred at −15° to −20° C. for 1.5 hours and then quenched by adding 25 ml of water. The biphasic mixture is warmed to ambient temperature and stirred for 2 hours. The layers are separated and the aqueous extracted with 25 ml of dichloromethane. The organic extracts are combined and washed twice with 25 ml of saturated aqueous sodium bicarbonate, and once each with 25 ml of 1 N HCl, 25 ml of saturated sodium chloride, and 25 ml of water. The washed organic solution is dried over anhydrous sodium sulfate, filtered and then concentrated to an oil by vacuum distillation. The oil is reconstituted with 25 ml of methyl t-butyl ether and 4.8 ml of methanol. Then a solution of chlorotrimethylsilane (1.28 g, 11.9 mmol) in 7.5 ml of methyl t-butyl ether resultant solution is added dropwise to produce a thick slurry. The mixture is stirred at ambient temperature for 30 minutes, and filtered. The isolated cake is washed twice with 10 ml of methyl t-butyl ether, and dried overnight under vacuum at 50° C. to provide 2.42 g of PNU-280715A (9.77 mmol, 41%) as a yellow powder.

Chiral HPLC is performed using a Chiralcel OD 250×4.6 mm column eluted at 0.5 ml/min. with a solvent mixture consisting of 25% vol. isopropanol, 75% vol. n-heptane and 0.1% vol. diethylamine. The (R)-enantiomer eluted at 17.2 min. and the (S)-enantiomer eluted at 24.6 min. Using this method, the ratio of enantiomers for the isolated PNU-280715A was determined to be 99.5: 0.5, giving an enantiomeric excess of 99% for the product.

Preparation 3 4-Nitroso-3-phenyl-3,4-dihydro-2H-1,4-benzoxazine

To a mixture of 3-phenyl-3,4-dihydro-2H-1,4-benzoxazine (17 g, 80.5 mmol) in ethyl ether (100 mL) is added trifluoroacetic acid (6.2 mL 80.5 mmol). The resulting solution is chilled to 5° C. in an ice bath, to which n-butyl nitrite (9.4 mL 80.5 mmol) is added dropwise. The mixture is stirred for 1 h and transferred to a separatory funnel to which is slowly added potassium carbonate (2.6 g, 18.8 mmol) in water (200 mL). Solids formed in the ether layer. The layers are separated and ethyl ether (100 mL) is added to dissolve the solids. The ether layer is washed twice with water (200 mL), dried over magnesium sulfate, filtered and concentrated. The resulting oil is chilled in the refrigerator overnight. The solids formed from the oil are ground-up in hexanes and collected by filtration to give 15.7 g (81%) of 4-nitroso-3-phenyl-3,4-dihydro-2H-1,4-benzoxazine.

IR (drift) 1493, 1467, 1438, 1321, 1305, 1288, 1243, 1230, 1151, 1118, 1062, 763, 754, 735, 728 cm$^{-1}$; $^1$H NMR (CDCl$_3$) δ 4.23, 4.56, 6.02, 7.1, 7.2, 7.3, 8.2. Anal. Calcd for C$_{14}$H$_{12}$N$_2$O$_2$: C, 69.99; H, 5.03; N, 11.66. Found: C, 69.86; H, 5.07; N, 11.57.

Preparation 4 3-Phenyl-2,3-dihydro-4H-1,4-benzoxazin-4-ylamine

A slurry of lithium aluminum hydride (4.9 g, 130.5 mmol) in ethyl ether (100 mL) is stirred at ice bath temperature under an argon atmosphere. A solution of 4-nitroso-3-phenyl-3,4-dihydro-2H-1,4-benzoxizine in ethyl ether (300 mL) is added dropwise over 1 h. The mixture is removed from the ice bath and allowed to stir for 18 h. Water (50 mL) is slowly added forming solids. The solids are collected by filtration and washed with ethyl ether. The resulting filtrates are combined and washed three times with water (200 mL), dried over magnesium sulfate, and concentrated to give 8.7 g (61%) of 3-phenyl-2,3-dihydro-4H-1,4-benzoxazin-4-ylamine.

IR (liq.) 1585, 1491, 1462, 1453, 1351, 1309, 1283, 1267, 1243, 1215, 1046, 814, 750, 728, 702 cm$^{-1}$; $^1$H NMR (CDCl$_3$) δ 3.25, δ 4.27, 6.83, 6.92, 7.41. Anal. Calcd for C$_{14}$H$_{14}$N$_2$O: C, 74.31; H, 6.24; N, 12.38. Found: C, 74.48; H, 6.28; N, 11.77.

Preparation 5 1-Phenyl-1,2,9,10-tetrahydro[1,4]oxazino[2,3,4-jk]carbazol-7(8H)-one To a mixture of 3-phenyl-2,3-dihydro-4H-1,4-benzoxazin-4-ylamine (1.042 g, 4.6 mmol) in toluene (30 mL) is added, with stirring, cyclohexane-1,3-dione (0.538 g, 4.8 mmol). The mixture is heated at 85° C. for 15 min, at which time p-toluenesulfonic acid monohydrate (0.874 g, 4.6 mmol) is added and the temperature increased to 110° C. The mixture is refluxed for 24 h, cooled to room temperature and concentrated. The residue is partitioned between CH$_2$Cl$_2$/1N NaOH and the organic layer is washed with brine and dried over magnesium sulfate. Column chromatography (100 g silica gel) using (acetone/hexane (25/75)) as eluent gave 0.475 g (34%) of 1-phenyl-1,2,9,10-tetrahydro [1,4]oxazino[2,3,4-jk]carbazol-7(8H)-one.

IR (drift) 1629, 1492, 1458, 1444, 1409, 1358, 1320, 1262, 1245, 1194, 1129, 784, 755, 736, 704 cm$^{-1}$; $^1$H NMR (CDCl$_3$) δ 2.1, 2.4, 2.5, 2.6, 4.5, 5.4, 6.8, 7.1, 7.2, 7.4, 7.8. Anal. Calcd for C$_{20}$H$_{17}$NO$_2$: C, 79.18; H, 5.65; N, 4.62. Found: C, 78.85; H, 5.83; N, 4.63.

Preparation 6 Resolution of 1-Phenyl-1,2,9,10-tetrahydro[1,4]oxazino[2,3,4-jk]carbazol-7(8H)-one 1-Phenyl-1,2,9,10-tetrahydro[1,4]oxazino[2,3,4-jk] carbazol-7(8H)-one (0.600 g) is dissolved in a minimum volume of chloroform and isopropanol is added to give a final volume of 15 mL. The solution is injected onto a 5×50 cm column of 20 micron Chiralcel OD (Chiral Technologies) held at 30° C. The sample is eluted with 30% isopropanol in heptane (V/V) at 75 mL/min while monitoring at 245 nm using a Merck/Sepracor ST-140 HPLC with closed loop peak shaving and recycling capability. About 70% of the front part of the broad peak that eluted between 25–32 minutes is collected and about 40% of the tail of the second peak that eluted between 29–37 minutes is collected. The central portions of these overlapping peaks are recycled and complete resolution is obtained on the second pass. The appropriate fractions are pooled and the solvent is removed on a rotary evaporator. The residues are assayed on a 0.46×25 cm Chiralcel OD-H column at ambient temperature using 25% isopropanol in heptane at 0.5 mL/min and detection at 244 nm. The earlier eluting enantiomer (0.297 g, $R_t$=21.7 min) assayed for 97.6% ee. Chromatography on silica gel using acetone/hexane (20/80) gave 0.296 g of (R)-(−)-1-phenyl-1,2,9,10-tetrahydro[1,4]oxazino[2,3,4-jk] carbazol-7(8H)-one; $[\alpha]_D$=−81° (CH$_2$Cl$_2$). The later eluting enantiomer (0.261 g, $R_t$=26.8 min) assayed for >99% ee. Chromatography on silica gel using acetone/hexane (20/80) gave 0.254 g of (S)-(+)-1-phenyl-1,2,9,10-tetrahydro[1,4] oxazino[2,3,4-jk]carbazol-7(8H)-one. $[\alpha]_D$=+84° (CH$_2$Cl$_2$).

Preparation 7 (S)-(+)-1-Phenyl-1,2-dihydro[1,4]oxazino[2,3,4-jk]carbazol-7-ol

A mixture of (S)-(+)-1-phenyl-1,2,9,10-tetrahydro[1,4] oxazino[2,3,4-jk]carbazol-7(8H)-one (0.397 g, 1.31 mmol), cupric chloride dihydrate (0.513 g, 3.01 mmol), and acetic acid/water (1:1, 4 mL) is heated at 120° C. for 6 h. After cooling, the mixture is partitioned between dichloromethane, water, and aq. sodium bicarbonate. The organic layers are filtered through sodium sulfate, concentrated, and stored over the weekend in the freezer. The mixture is then stirred at 130–140° C. with lithium carbonate (0.106 g, 1.44 mmol), lithium chloride (0.061 g, 1.44 mmol), and DMF (3 mL). After cooling, the mixture is partitioned between dichloromethane and sat'd aq. ammonium chloride. The organic layers are dried over sodium sulfate, concentrated, and the residue is chromatographed on silica gel gel (60 mL) using ethyl acetate/hexane (10/90) to give 0.184 g (47% for both steps) of (S)-(+)-1-phenyl-1,2-dihydro[1,4]oxazino[2,3,4-jk]carbazol-7-ol. $[\alpha]_D$=+98° (MeOH).

Preparation 8 (S)-(+)-2-[(1-Phenyl-1,2-dihydro[1,4]oxazino[2,3,4-jk]carbazol-7-yl)oxy]acetonitrile A mixture of (S)-(+)-1-Phenyl-1,2-dihydro[1,4]oxazino[2,3,4-jk]carbazol-7-ol (0.161 g, 0.534 mmol), bromoacetonitrile (0.074 mL, 1.07 mmol), potassium carbonate (0.148 g, 1.07 mmol), and DMF (2 mL) is stirred at 70° C. for 4 h. Additional bromoacetonitrile (0.074 mL) and potassium carbonate (0.074 g) are then added and the mixture is stirred overnight. Bromoacetonitrile and potassium carbonate (0.074 mL and 0.074 g, respectively) are then added and the temperature is increased to 90° C. The mixture is heated at that temperature for 5.5 h and then allowed to cool and stir overnight, after which the mixture is partitioned between ethyl acetate, aq. ammonium chloride, and brine. The organic layers are dried over magnesium sulfate, concentrated, and the residue is chromatographed on silica gel gel (40 mL) using first CH$_2$Cl$_2$/hexane (1:1) to elute unreacted starting material, and then ethyl acetate/CH$_2$Cl$_2$/hexane (5:45:50) to give 0.113 g of (S)-(+)-2-[(1-phenyl-1,2-dihydro[1,4]oxazino[2,3,4-jk]carbazol-7-yl)oxy]acetonitrile.

$[\alpha]_D$=118° (CH$_2$Cl$_2$). Anal. Calcd for C$_{22}$H$_{16}$N$_2$O$_2$: C, 77.63; H, 4.74; N, 8.23. Found: C, 77.36; H, 4.99; N, 8.23.

Example 1

(S)-(+)-[(1-Phenyl-1,2-dihydro[1,4]oxazino[2,3,4-jk] carbazol-7-yl)oxy]ethanamine

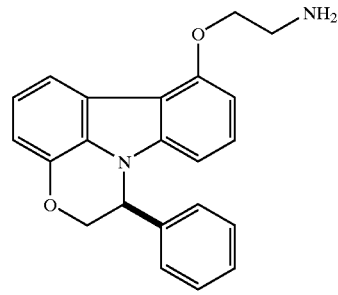

A mixture of (S)-(+)-2-[(1-phenyl-1,2-dihydro [1,4] oxazino[2,3,4-jk]carbazol-7-yl)oxy]acetonitrile (0.928 g, 0.273 mmol), borane-methyl sulfide complex (0.10 mL, 1.09 mmol), and dry THF (2 mL) is stirred at reflux for 2 h. After cooling, methanol is cautiously added to quench excess borane. The mixture is taken to dryness in vacuo and methanol is again added and removed. Dichloromethane and methanol are added to the residue and about 10 drops of conc. HCl are added. The mixture is stirred for 1 h and then taken to dryness in vacuo. The residue is partitioned between dichloromethane and aq. sodium bicarbonate. The organic layers are dried over sodium sulfate and concentrated. The residue is chromatographed on silica gel (17 mL) using methanol/dichloromethane/ammonium hydroxide (2/98/0.1%) to give 0.0774 g (82%) of (S)-(+)-[(1-phenyl-1,2-dihydro[1,4]oxazino[2,3,4-jk]carbazol-7-yl)oxy] ethanamine.

$[\alpha]_D$=+95°; $^1$H NMR (CDCl$_3$) δ 1.57, 3.28, 4.26, 4.50–4.66, 5.52, 6.45, 6.65, 6.96, 7.16, 7.34, 7.85. Anal. Calcd for C$_{22}$H$_{20}$N$_2$O$_2$: C, 76.72; H, 5.85; N, 8.13. Found: C, 76.16; H, 6.12; N, 7.90.

Preparation 9 (R)-(−)-1Phenyl-1,2-dihydro[1,4]oxazino[2,3,4-jk]carbazol-7-ol

To (R)-(−)-1-phenyl-1,2,9,10-tetrahydro[1,4]oxazino[2,3,4-jk]carbazol-7(8H)-one (17.3 g, 57.3 mmol) in dry DMF (60 mL) is added anhydrous cupric chloride (17.7 g 131.8 mmol) and anhydrous lithium chloride (9.6 g, 229 mmol). The mixture is heated at 60° C. for 40 h. The mixture is then poured into water (600 mL), forming solids. The solids are dissolved in ethyl acetate (50 mL) and filtered to remove inorganic solids. The filtrates are concentrated to dryness and the resulting solids are dissolved in DMF (60 mL), to which is added lithium bromide (12.4 g, 143 mmol) and lithium carbonate (10.6 g, 143 mmol). The mixture is heated at 120° C. for 6 h, cooled, then partitioned between water and CH$_2$Cl$_2$, and the organic layer washed three times with water (200 mL). Column chromatography (600 mL silica) is performed using EtOAc/hexanes (20/80) as eluent. The material is then rechromatographed (600 mL silica) using EtOAc/hexane (20/80) as eluent to give 6.0 g (35%) of (R)-(−)-1-phenyl-1,2-dihydro[1,4]oxazino[2,3,4-jk] carbazol-7-ol; $[\alpha]^{25}_D$=−121° (c 0.73, methylene chloride).

$^1$H NMR (CDCl$_3$) δ 4.5, 4.6, 5., 6.4, 6.6, 7.0, 7.1, 7.2, 7.3, 7.8. Anal. Calcd for C$_{20}$H$_{15}$NO$_2$: C, 79.71; H, 5.02; N, 4.65. Found: C, 78.82; H, 5.14; N, 4.50.

Preparation 10 (R)-(−)-2-[(1-phenyl-1,2-dihydro[1,4] oxazino[2,3,4-jk]carbazol-7-yl)oxy]acetonitrile To a mixture of (R)-(−)-1-phenyl-1,2-dihydro[1,4] oxazino[2,3,4-jk]carbazol-7-ol (5.9 g 19.6 mmol) in DMF (50 mL) is added potassium carbonate (8.1 g, 58.7 mmol) and bromoacetonitrile (4.1 mL, 58.7 mmol). The mixture is stirred at room temperature for 20 h. The mixture is partitioned between water and Et$_2$O. The organic layer is washed twice with water (200 mL), dried over anhydrous sodium sulfate and concentrated. Column chromatography (800 mL silica) using CH$_2$Cl$_2$ eluent gave 5.94 g (89%) of (R)-(−)-2-[(1-phenyl-1,2-dihydro[1,4]oxazino[2,3,4-jk]carbazol-7-yl)oxy]acetonitrile.

$[\alpha]^{25}_D$=−115° (c 0.84, methylene chloride); IR (drift) 1586, 1497, 1456, 1452, 1321, 1311, 1262, 1237, 1177, 1152, 1041, 789, 738, 718, 700 cm$^{-1}$; $^1$H NMR (CDCl$_3$) δ 4.5, 4.6, 5.0, 5.5, 6.5, 6.7, 7.0, 7.2, 7.3, 7.8. Anal. Calcd for C$_{22}$H$_{16}$N$_2$O$_2$: C, 77.63; H, 4.74; N, 8.23 Found: C, 76.75; H, 4.72; N, 8.10.

Example 2

(R)-(−)-[(1-Phenyl-1,2-dihydro[1,4]oxazino[2,3,4-jk]carbazol-7-yl)oxy]ethanamine and its Methanesulfonic Acid Salt

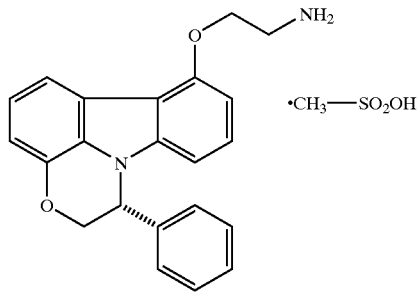

To a mixture of (R)-(−)-2-[(1-phenyl-1,2-dihydro[1,4]oxazino[2,3,4-jk]carbazol-7-yl)oxy]acetonitrile (5.94 g, 17.45 mmol) in THF (100 mL) is added borane-methylsulfide complex (4.97 mL, 52.35 mmol). The mixture is refluxed at 85° C. for 24 h. The mixture is removed from heat and methanol is slowly added until gas evolution ceased. The solvents are removed under vacuum. Methanol (10 mL) is added and then removed under vacuum. The residue is then dissolved in CH$_2$Cl$_2$/CH$_3$OH (1:2, 75 mL). Conc. HCl (10 mL) is added and the mixture is heated at 65° C. for 2.5 h. The mixture is removed from heat and neutralized with aqueous potassium carbonate. The mixture is then partitioned between water and CH$_2$Cl$_2$ and the organic layer is washed twice with water (200 mL) and dried over anhydrous sodium sulfate, then concentrated. Column chromatography (450 mL silica) using CH$_3$OH/CH$_2$Cl$_2$ (8:92) as eluent gave 5.85 g (97%) of (R)-(−)-[(1-phenyl-1,2-dihydro[1,4]oxazino[2,3,4-jk]carbazol-7-yl)oxy]ethanamine, which is converted to the methanesulfonic acid salt to give 4.25 g (55%) of (R)-(−)-[(1-phenyl-1,2-dihydro[1,4]oxazino[2,3,4-jk]carbazol-7-yl)oxy]ethanamine methanesulfonic acid salt.

mp 236° C.; $[\alpha]^{25}_D$=−37° (c 0.96, DMSO); IR (drift) 2991, 2939, 1589, 1456, 1451, 1265, 1241, 1223, 1202, 1183, 1152, 1043, 791, 735, 701 cm$^{-1}$; $^1$H NMR (DMSO-d$_6$) δ 2.69, 3.47, 4.4, 4.5, 5.5, 6.4, 6.6, 6.8, 7.0, 7.1, 7.2, 7.8. Anal. Calcd for C$_{22}$H$_{20}$N$_2$O$_2$·CH$_4$O$_3$S: C, 62.71; H, 5.49; N, 6.36; S, 7.28. Found: C, 62.42; N, 6.27.

Preparation 12 8-Chloro-1-phenyl-1,2,9,10-tetrahydro[1,4]oxazino[2,3,4-jk]carbazol-7(8H)-one A mixture of 1-phenyl-1,2,9,10-tetrahydro[1,4]oxazino[2,3,4-jk]carbazol-7(8H)-one (0.441 g, 1.45 mmol), anhydrous CuCl$_{12}$ (0.430 mmol, 3.20 mmol), anhydrous LiCl (0.308 g, 7.27 mmol), and DMF (3 mL) is stirred at 65° C. for 50 h. After cooling, the mixture is stored in the refrigerator overnight and then partitioned between CH$_2$Cl$_2$ and brine. The organic layers are dried over sodium sulfate and taken to dryness. Chromatography on silica gel gel (60 mL) using ethyl acetate/CH$_2$Cl$_2$/hexane (5:45:50) gave 0.349 g (71%) of 8-chloro-1-phenyl-1,2,9,10-tetrahydro[1,4]oxazino[2,3,4-jk]carbazol-7(8H)-one (mixture of diastereomers).

Isomer 1: R$_f$(EtOAc/CH$_2$Cl$_2$/hexane (5:45:50): 0.33; MS (ESI+) m/z 338 (M+H)$^+$; $^1$H NMR (CDCl$_3$) δ 2.44, 3.00, 4.50–4.63, 5.42, 6.82, 7.04, 7.21, 7.37, 7.78. Isomer 2: R$_f$ (EtOAc/CH$_2$Cl$_2$/hexane (5:45:50): 0.21; MS (ESI+) m/z 338 (M+H)$^+$; $^1$H NMR (CDCl$_3$) δ 2.30–2.75, 4.45–4.60, 5.40, 6.82, 7.13, 7.21, 7.41, 7.77.

Preparation 13 1-Phenyl-1,2-dihydro[1,4]oxazino[2,3,4-jk]carbazol-7-ol

Method A:

A mixture of 8-chloro-1-phenyl-1,2,9,10-tetrahydro[1,4]oxazino[2,3,4-jk]carbazol-7(8H)-one (0.235 g, 0.697 mmol), anhydrous LiCl (0.0355 g, 0.837 mmol), Li$_2$CO$_3$ (0.0618 g, 0.837 mmol), and DMF (1.8 mL) is stirred at 140° C. for 3.5 h. After cooling, the mixture is partitioned between CH$_2$Cl$_2$ and water. The organic layers are dried over sodium sulftate, concentrated, and chromatographed on silica gel gel using EtOAc/hexane (10/90) to give 0.143 g (68%) of 1-phenyl-1,2-dihydro[1,4]oxazino[2,3,4-jk]carbazol-7-ol.

Method B:

To 1-phenyl-1,2,9,10-tetrahydro[1,4]oxazino[2,3,4-jk]carbazol-7(8H)-one (4.0 g, 13.19 mmol) in ethyl acetate/acetonitrile (30 mL/15 mL) is added trifluoroacetic acid (2 mL) and anhydrous cupric chloride (3.56 g, 26.4 mmol). The mixture is heated to reflux at 80° C. for 1.5 h. The mixture is concentrated. The residue is dissolved in ethyl acetate (50 mL) and filtered to remove inorganic solids. The filtrates are washed with saturated potassium carbonate solution followed by water, dried over magnesium sulfate and concentrated. The residue is dissolved in DMF (15 ml) to which is added lithium bromide (2.4 g, 27.7 mmol) and lithium carbonate (2.04 g, 27.7 mmol). The mixture is heated at 120° C. for 4.5 h then partitioned between water and CH$_2$Cl$_2$ with the organic layer being washed twice with brine (30 mL). Column chromatography (200 g silica gel) using EtOAc/hexanes (20/80) as eluent gave 1.05 g (26%) of 1-phenyl-1,2-dihydro[1,4]oxazino[2,3,4-jk]carbazol-7-ol.

$^1$H NMR (CDCl$_3$) δ 4.5, 4.6, 5.5, 6.4, 6.6, 7.0, 7.1, 7.2, 7.3, 7.8.

Method C:

Water is decanted from wet Raney nickel (2.5 g) and toluene is added and additional water is azeotroped off under vacuum. Toluene and decalin (4 mL) are added to the damp Raney nickel and toluene is again azeotroped off. 1-Phenyl-1,2,9,10-tetrahydro[1,4]oxazino[2,3,4-jk]carbazol-7(8H)-one (0.180 g, 0.593 mmol) is added and the mixture is heated at 180° C. (additional toluene/water azeotroping occurs). After 3 h, the mixture is cooled. Dichloromethane is added and the Raney nickel is removed by filtration. The filtrate is concentrated under vacuum until solids begin precipitating out. Hexane is added and the mixture is stored in the rcfrigerator overnight. The solids are then collected by filtration (wash with hexane) and chromatographed on silica gel gel (30 mL) using ethyl acetate/hexane (20/80) to give 0.119 g (66%) of 1-phenyl-1,2-dihydro[1,4]oxazino[2,3,4-jk]carbazol-7-ol.

$^1$H NMR (CDCl3) δ 6 4.50–4.65, 5.36, 5.51, 6.41, 6.56, 6.97, 7.09, 7.20, 7.35, 7.84. Anal. Calcd for C$_{20}$H$_{15}$NO$_2$: C, 79.71; H, 5.02; N, 4.65. Found: C, 79.33; H, 5.10; N, 4.63.

Method D:

A mixture of 1-phenyl-1,2,9,10-tetrahydro[1,4]oxazino[2,3,4-jk]carbazol-7(8H)-one (0.0586 g, 0.193 mmol) and 10% Pd/C (0.058 g) in 2-(ethoxyethoxy)ethanol (1 mL) is heated at 190–200° C. for 4 h and then cooled and partitioned between dichloromethane and water. The organic layers are dried over magnesium sulfate, filtered, and the filtrate is concentrated and the residue chromatographed on silica gel using ethyl acetate/hexane (20/80) to give 0.0274 g of 1-phenyl-1,2-dihydro[1,4]oxazino[2,3,4-jk]carbazol-7-ol.

$^1$H NMR (CDCl$_3$) δ 4.57, 5.37, 5.50, 6.42, 6.56, 6.98, 7.09, 7.17, 7.35, 7.84.

Preparation 14 2-[(1-Phenyl-1,2-dihydro[1,4]oxazino[2,3,4-jk]carbazol-7-yl)oxy]acetonitrile To a mixture of 1-phenyl-1,2-dihydro[1,4]oxazino[2,3,4-jk]carbazol-7-ol (1.05 g 3.49 rumol) in DMF (15 mL) is added potassium carbonate (2.4 g, 17.4 mmol) and bromoacetonitrile (1.2 mL, 17.4 mmol). The mixture is heated at 85° C. for 1.5 h. The mixture is cooled and partitioned between water and Et$_2$O. The organic layer is washed twice with water (200 mL), dried over magnesium sulfate and concentrated. Column chromatography (60 g silica gel) using CH$_2$Cl$_2$ as eluent gave 1.1 g (92%) of 2-[(1-phenyl-1,2-dihydro[1,4]oxazino[2,3,4-jk]carbazol-7-yl)oxy]acetonitrile.

mp 61° C.; IR (drift) 1587, 1496, 1460, 1452, 1432, 1321, 1311, 1262, 1237, 1152, 1042, 790, 738, 718, 700 cm$^{-1}$; $^1$H NMR (CDCl$_3$) δ 4.5, 4.6, 5.0, 5.5, 6.5, 6.7, 7.0, 7.2, 7.3, 7.8.

Example 3

N,N-Diethyl-2-[(1-phenyl-1,2-dihydro[1,4]oxazino[2,3,4-jk]carbazol-7-yl)oxy]-1-ethanamine and its Maleic Acid Salt

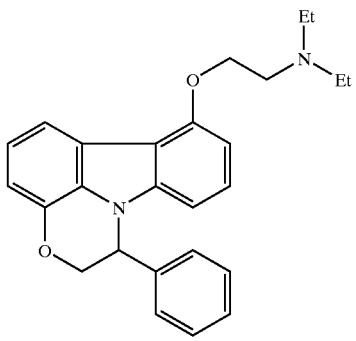

To a mixture of 1-phenyl-1,2-dihydro[1,4]oxazino[2,3,4-jk]carbazol-7-ol (0.048 g, 0.159 mmol), potassium carbonate (0.044 g, 0.318 mmol), and DMF (1.0 mL) at 100° C. is added diethylaminoethyl chloride hydrochloride (0.033 g, 0.191 mmol) in aliquots over 1 h. After 5.5 h, an additional 0.011 g of diethylaminoethyl chloride hydrochloride is added, and one hour later, a few crystals of sodium iodide are added. After heating for ten hours, the mixture is allowed to stir at room temperature for the remainder of the night. Additional potassium carbonate (0.022 g) and diethylarminoethyl chloride hydrochloride (0.017 g) are added and the mixture is stirred at 100° C. for 1.5 h. The major portion of the DMF is distilled off and the residue is partitioned between dichloromethane and water. The organic layers are dried over sodium sulfate and concentrated. The residue is chromatographed on silica gel (17 mL) using EtOAc/dichloromethane (30/70 to 60/40) to give 0.040 g of N,N-diethyl-2-[(1-phenyl-1,2-dihydro[1,4]oxazino[2,3,4-jk]carbazol-7-yl)oxy]-1-ethanamine.

MS (ESI+) m/z 401 (M+H)$^+$; $^1$H NMR (CDCl$_3$) δ 1.13, 2.73, 3.10, 4.31, 4.58, 5.51, 6.44, 6.65, 6.95, 7.15, 7.34, 7.88.

The maleic acid salt is prepared using maleic acid and crystallized from EtOH to give N,N-diethyl-2-[(1-phenyl-1,2-dihydro[1,4]oxazino[2,3,4-jk]carbazol-7-yl)oxy]-1-ethanamine, maleic acid salt. mp 105–107° C. Anal. Calcd for C$_{26}$H$_{26}$N$_2$O$_2$·C$_4$H$_4$O$_4$: C, 69.75; H, 6.24; N, 5.42. Found: C, 69.32; H, 6.37; N, 5.28.

Example 4

[(1-Phenyl-1,2-dihydro[1,4]oxazino[2,3,4-jk]carbazol-7-yl)oxy]ethanamine and its Methanesulfonic Acid Salt

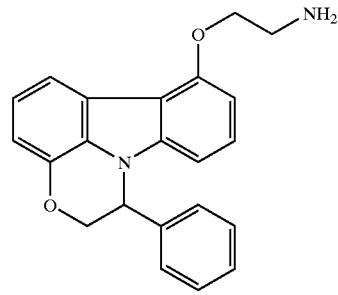

To a solution of 2-[(1-phenyl-1,2-dihydro[1,4]oxazino[2,3,4-jk]carbazol-7-yl)oxy]acetonitrile (0.380 g, 1.12 mmol) in dry THF (5 mL) is added borane-methyl sulfide complex (0.317 mL, 3.35 mmol). The mixture is stirred at 75° C. for 3 h; after cooling, methanol is cautiously added to quench excess borane-methyl sulfide complex. When gas evolution had ceased, the mixture is concentrated to dryness and methanol is again added and the mixture is allowed to stir overnight. Additional methanol and enough CH$_2$Cl$_2$ to dissolve the solids is added, followed by conc. HCl (0.1 mL). The mixture is stirred for 2 h, then concentrated and partitioned between CH$_2$Cl$_2$ and aq. sodium bicarbonate. The organic layers are taken to dryness (sodium sulfate) to give 0.307 g (80%) of [(1-phenyl-1,2-dihydro[1,4]oxazino[2,3,4-jk]carbazol-7-yl)oxy]ethanamine.

$^1$H NMR (CDCl$_3$) δ 1.6, 3., 4.26, 4.50–4.66, 5.52, 6.45, 6.65, 6.96, 7.16 m, 7.34, 7.85. Addition of methanesulfonic acid (0.0857 g, 0.891 mmol) to a methylene chloride solution of the above gave, after crystallization from methanol, 0.328 g of [(1-phenyl-1,2-dihydro[1,4]oxazino[2,3,4-jk]carbazol-7-yl)oxy]ethanamine, methanesulfonate salt.

Anal. Calcd for C$_{22}$H$_{20}$N$_2$O$_2$·CH$_4$O$_3$S: C, 62.71; H, 5.49; N, 6.36. Found: C, 62.63; H, 5.56; N, 6.29.

Example 5

N-isopropyl-N-{2-[(1-phenyl-1,2-dihydro[1,4]oxazino[2,3,4-jk]carbazol-7-yl)oxy]ethyl}amine and its Maleic Acid Salt

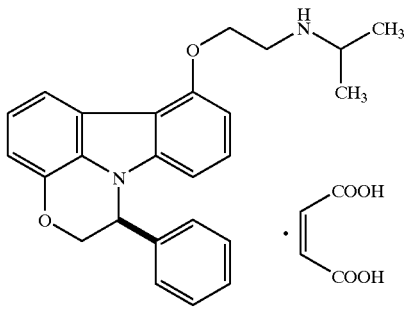

To a solution of 2-[(1-phenyl-1,2-dihydro[1,4]oxazino[2,3,4-jk]carbazol-7-yl)oxy]acetonitrile (0.497 g, 1.46 mmol) in dry THF is added borane-methyl sulfide complex (0.42 mL, 4.38 mmol). The mixture is stirred at 80° C. for 1.75 h and then allowed to cool. Methanol is carefully added to decompose excess borane. The solution is taken to dryness in vacuo and the addition and removal of methanol is repeated. Acetone (12 mL) and 0.5 N HCl (6 mL) are added and the to the residue and the mixture is stirred at 65–70° C. for 15 min. Acetone is removed in vacuo and the residue is partitioned between dichloromethane and aq. sodium bicarbonate. The organic layer is dried over sodium sulfate, concentrated, and chromatographed on silica gel (100 mL) using methanol/dichloromethane (2/98) as eluant to give 0.278 g of [(1-phenyl-1,2-dihydro[1,4]oxazino[2,3,4-jk]carbazol-7-yl)oxy]ethanamine and 0.24 g of material which, after resubjection to borane-methyl sulfide, remained largely unchanged by TLC. Chromatography on silica gel (60 mL) using methanol/dichloromethane/ammonium hydroxide (2/98/0.1%) gave 0.068 g of N-{2-[(1-phenyl-1,2-dihydro[1,4]oxazino[2,3,4-jk]carbazol-7-yl)oxy]ethyl}-2-propanamine.

$^1$H NMR (CDCl$_3$)δ 1.8, 1.17, 3.01, 3.221, 4.35, 4.49–4.65, 5.51, 6.44, 6.66, 6.97, 7.16, 7.34, 7.82.

The maleic acid salt is prepared using maleic acid (0.0204 g maleic acid, crystallization from dichloromethane/methanol/hexane) to give N-{2-[(1-phenyl-1,2-dihydro[1,4]oxazino[2,3,4-jk]carbazol-7-yl)oxy]ethyl}-2-propanamine, maleic acid salt. Anal. Calcd for C$_{25}$H$_{26}$N$_2$O$_2$·C$_4$H$_4$O$_4$: C, 69.31; H, 6.02; N, 5.57. Found: C, 69.30; H, 6.16; N,5.65.

Preparation 15 N-{2-[(1-Phenyl-1,2-dihydro[1,4]oxazino[2,3,4-jk]carbazol-7-yl)oxy]ethyl}acetamide

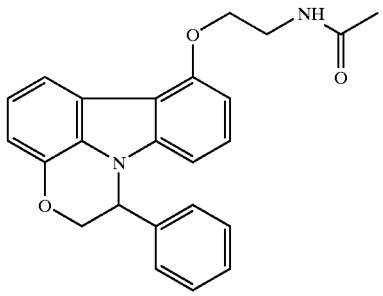

To a mixture of [(1-phenyl-1,2-dihydro[1,4]oxazino[2,3,4-jk]carbazol-7-yl)oxy]ethanamine (0.58 g, 1.68 mmol) in DMF (10 mL) is added acetic anhydride (0.17 g, 1.68 mmol) and DMAP (0.01 g, 0.082 mmol). The mixture is heated at 85° C. for 45 min, then partitioned between water and ether. The organic layer is washed twice with water, dried over magnesium sulfate and concentrated. Column chromatography (70 g silica gel) using CH$_2$Cl$_2$/acetone (80/20) as eluent gave 0.46 g (71%) of N-{2-[(1-phenyl-1,2-dihydro[1,4]oxazino[2,3,4-jk]carbazol-7-yl)oxy]ethyl}acetamide.

$^1$H NMR (CDCl$_3$) δ 2., 3.9, 4.3, 4.5, 4.6, 5.5, 6.5, 6.6, 7.0, 7.2, 7.3, 7.8.

Example 6

N-Ethyl-2-[(1-phenyl-1,2-dihydro[1,4]oxazino[2,3,4-jk]carbazol-7-yl)oxy]-1-ethanamine and its Maleic Acid Salt

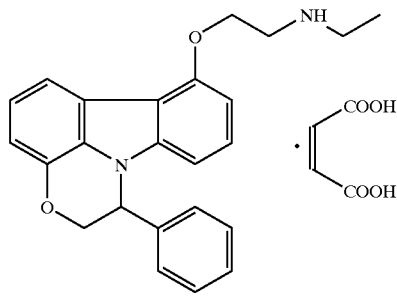

To a mixture of N-{2-[(1-phenyl-1,2-dihydro[1,4]oxazino[2,3,4-jk]carbazol-7-yl)oxy]ethyl}acetamide (0.46 g, 1.19 mmol) in dry THF (10 mL) is added borane-methylsulfide complex (0.34 mL, 3.6 mmol). The mixture is refluxed under an argon atmosphere at 85° C. for 18 h. The mixture is then cooled to room temperature and methanol is slowly added until gas evolution ceased. The solvents are removed and methanol (20 mL) is added and then removed. The residue is dissolved in methanol (20 mL), CH$_2$Cl$_2$ (3 mL), and conc. HCl (3 mL) and then heated at 65° C. for 45 min. The mixture is neutralized with aqueous potassium carbonate and partitioned between water and CH$_2$Cl$_2$. The organic layer is washed with water, dried over magnesium sulfate and concentrated. Column chromatography (50 g silica gel) using CH$_3$OH/CH$_2$Cl$_2$ (4/96) as eluent and gave 0.268 g (61%) of a colorless oil, N-ethyl-2-[(1-phenyl-1,2-dihydro[1,4]oxazino[2,3,4-jk]carbazol-7-yl)oxy]-1-ethanamine. Conversion to the maleic acid salt gave 0.1993 g (34%) of N-ethyl-2-[(1-phenyl-1,2-dihydro[1,4]oxazino[2,3,4-jk]carbazol-7-yl)oxy]-1-ethanamine, maleic acid salt; mp 105° C.

IR (drift) 1634, 1609, 1585, 1532, 1496, 1452, 1379; 1350, 1261, 1240, 1152, 1042, 865, 790, 739 cm$^{-1}$; $^1$H NMR (CDCl$_3$) δ 1.4, 3.3, 3.6, 4.5,4.6, 6.1, 6.4, 6., 6.9, 7.1, 7.3, 7.8. Anal. Calcd for C$_{24}$H$_{24}$N$_2$O$_2$·C$_4$H$_4$O$_4$: C, 68.84; H, 5.78; N, 5.73. Found: C, 68.50; H, 5.88; N, 5.66.

Example 7

2-[(1-Phenyl-1,2-dihydro[1,4]oxazino[2,3,4-jk]carbazol-7-yl)oxy]ethylformamide

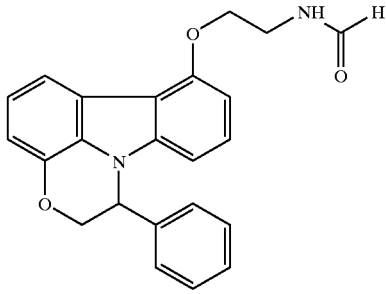

To a mixture of [(1-phenyl-1,2-dihydro[1,4]oxazino[2,3,4-jk]carbazol-7-yl)oxy]ethanamine (0.7423 g, 2.16 mmol) in $CH_2Cl_2$ (10 mL) is added ethylformate (2 mL). The mixture is heated for 2 h at 60° C., removed from heat and concentrated. Column chromatography (80 g silica gel) using $CH_3OH/CH_2Cl_2$ (4/96) gave 0.769 g (96%) of 2-[(1-phenyl-1,2-dihydro[1,4]oxazino[2,3,4-jk]carbazol-7-yl)oxy]ethylformamide.

IR (drift) 1668, 1637, 1585, 1496, 1451, 1379, 1323, 1311, 1264, 1240, 1151, 1042, 790, 739, 700 $cm^{-1}$; $^1$H NMR ($CDCl_3$) δ 3.9, 4.3, 4.5, 4.6, 5.5, 6.5, 6.6, 7, 7.2, 7.3, 7.8, 8.3. Anal. Calcd for $C_{23}H_{20}N_2O_3$: C, 74.18; H, 5.41; N, 7.52. Found: C, 73.32; H, 5.67; N, 7.03.

Example 8

N-Methyl-2-[(1-phenyl-1,2-dihydro[1,4]oxazino[2,3,4-jk]carbazol-7-yl)oxy]-1-ethanamine and its Maleic Acid Salt

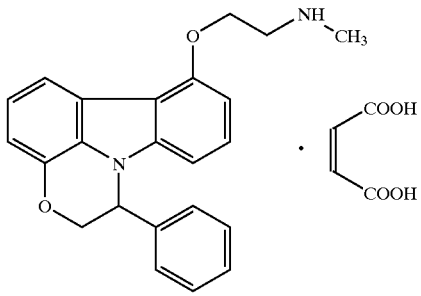

To a mixture of 2-[(1-phenyl-1,2-dihydro[1,4]oxazino[2,3,4-jk]carbazol-7-yl)oxy]ethylformamide (0.769 g, 2.06 mmol) in dry THF (10 mL) is added borane-methylsulfide complex (0.59 mL, 6.2 mmol). The mixture is refluxed at 85° C. under an argon atmosphere for 19.5 h. The mixture is then cooled to room temperature and methanol is slowly added until gas evolution ceased. The solvents are removed under vacuum and methanol (10 mL) is added and then removed. The mixture is dissolved in methanol (15 mL), $CH_2Cl_2$ (5 mL) and conc. HCl (4 mL) and then heated at 65° C. for 1.5 h. The mixture is then neutralized with aqueous potassium carbonate and partitioned between water/$CH_2Cl_2$. The organic layer is washed with water, dried over magnesium sulfate and concentrated. Column chromatography (80 g silica gel) using $CH_2Cl_2$/hexane/$CH_3OH$ (80/17/3) as eluent gave N-methyl-2-[(1-phenyl-1,2-dihydro[1,4]oxazino[2,3,4-jk]carbazol-7-yl)oxy]-1-ethanamine (0.536 g, 73%)

$^1$H NMR ($CDCl_3$) δ 2.61, 3.19, 4.35, 4.57, 5.52, 6.44, 6.66, 6.96, 7.16, 7.33, 7.81.

The compound is then converted to the maleic acid salt to give 0.4718 g (48%) of N-methyl-2-[(1-phenyl-1,2-dihydro[1,4]oxazino[2,3,4-jk]carbazol-7-yl)oxy]-1-ethanamine, maleic acid salt.

$^1$H NMR ($CDCl_3$) δ 2.9, 3.6, 4.5, 4.6, 5.5, 6.1, 6.4, 6.5, 6.9, 7.1, 7.3, 7.8. Anal. Calcd for $C_{23}H_{22}N_2O_2 \cdot C_4H_4O_4$: C, 68.34; H, 5.52; N, 5.90. Found: C, 68.32; H, 5.47; N, 5.90.

Preparation 16 8,8-Dichloro-1-phenyl-1,2,9,10-tetrahydro[1,4]oxazino[2,3,4-jk]carbazol-7(8H)-one To a mixture of 1-phenyl-1,2,9,10-tetrahydro[1,4]oxazino[2,3,4-jk]carbazol-7(8H)-one (0.5681 g, 1.87 mmol) in ethyl acetate (10 mL) and acetonitrile (10 mL) is added trifluoroacetic acid (2 mL,). Anhydrous cupric chloride (1.26 g, 9.36 mmol) is added and the mixture is heated to reflux at 95° C. for 2 h. After 5 h, additional anhydrous cupric chloride (0.63 g, 4.68 mmol) is added and the mixture is refluxed an additional hour. The mixture is then poured into $CH_2Cl_2$ (150 mL) and filtered. The filtrates are washed with aqueous potassium carbonate. The layers are separated and the organic layer is washed twice with water (200 mL), dried over magnesium sulfate and concentrated. Column chromatography (70 g silica gel) using ethyl acetate/$CH_2Cl_2$/hexane (5:45:50) gave 0.428 g (61%) of 8,8-dichloro-1-phenyl-1,2,9,10-tetrahydro[1,4]oxazino[2,3,4-jk]carbazol-7(8H)-one.

mp 104° C. $^1$H NMR ($CDCl_3$) δ 2.6, 2.8, 2.9, 4.5, 4.6, 5.4, 6.8, 7.1, 7.2, 7.4, 7.8. Anal. Calcd for $C_{20}H_{15}Cl_2NO_2$: C, 64.53; H, 4.06; N, 3.76; Cl, 19.05. Found: C, 64.47; H, 4.13; N, 3.73.

Preparation 17 8-Chloro-1-phenyl-1,2-dihydro[1,4]oxazino[2,3,4-jk]carbazol-7-ol

To a mixture of 8,8-dichloro-1-phenyl-1,2,9,10-tetrahydro[1,4]oxazino[2,3,4-jk]carbazol-7(8H)-one (0.4072 g, 1.09 mmol) in DMF (5 mL) is added lithium carbonate (0.242 g, 3.27 mmol) and lithium chloride (0.143 g, 3.39 mmol). The mixture is heated under an argon atmosphere at 120° C. for 1 h and then partitioned between water and $CH_2Cl_2$. The organic layer is washed twice with water (20 mL), dried over magnesium sulfate and concentrated. Column chromatography (50 g silica gel) using ethyl acetate/hexane (20/80) as eluent gave 0.2876 g (78%) of 8-chloro-1-phenyl-1,2-dihydro[1,4]oxazino[2,3,4-jk]carbazol-7-ol.

$^1$H NMR ($CDCl_3$) δ 4.5, 4.6, 5.5, 6.1, 6.3, 7.0, 7.2, 7.4, 7.9.

Preparation 18 2-[(8-Chloro-1-phenyl-1,2-dihydro[1,4]oxazino[2,3,4-jk]carbazol-7-yl)oxy]acetonitrile To a mixture of 8-chloro-1-phenyl-1,2-dihydro[1,4]oxazino[2,3,4-jk]carbazol-7-ol (0.286 g, 0.851 mmol) in DMF (5.0 mL) is added potassium carbonate (0.59 g, 4.25 mmol) and bromoacetonitrile (0.3 mL, 4.25 mmol). The mixture is heated at 85° C. for 1 h, then cooled and partitioned between water and $Et_2O$. The organic layer is washed three times with water (50 mL), dried over magnesium sulfate and concentrated. Column chromatography (60 g silica gel) using $CH_2Cl_2$/hexane (1/1) as eluent gave 0.2876 g (90%) of 2-[(8-chloro-1-phenyl-1,2-dihydro[1,4]oxazino[2,3,4-jk]carbazol-7-yl)oxy]acetonitrile.

$^1$H NMR ($CDCl_3$) δ 4.5, 4.6, 5.1, 5.5, 6.5, 7.0, 7.2, 7.4, 7.8.

Example 9

2-[(8-Chloro-1-phenyl-1,2-dihydro[1,4]oxazino[2,3,4-jk]carbazol-7-yl)oxy]-1-ethanamine and its Maleic Acid Salt

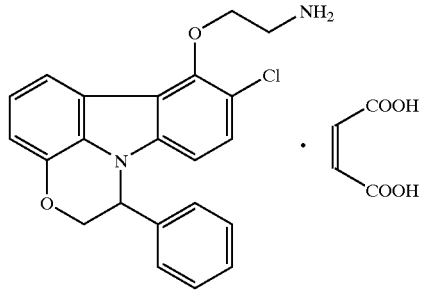

To a mixture of 2-[(8-chloro-1-phenyl-1,2-dihydro[1,4]oxazino[2,3,4-jk]carbazol-7-yl)oxy]acetonitrile (0.2838 g, 0.757 mmol) in dry THF (10 mL) is added borane-methylsulfide complex (0.22 mL, 2.27 mmol). The mixture is refluxed under an argon atmosphere at 82° C. for 18 h. The mixture is then cooled to room temperature and methanol is slowly added until gas evolution ceased. The solvents are removed under vacuum and methanol (5 mL) is added and again removed. The residue is dissolved in methanol (10 mL), $CH_2Cl_2$ (5 mL), and conc. HCl (3 mL) and heated at 60° C. for 1 h. The mixture is neutralized with aqueous potassium carbonate and partitioned between water and $CH_2Cl_2$. The organic layer is washed with water, dried over magnesium sulfate and concentrated. Column chromatography (50 g silica gel) using $CH_3OH/CH_2Cl_2$ (4/96) as eluent gave 0.080 g (28%) of 2-[(8-chloro-1-phenyl-1,2-dihydro[1,4]oxazino[2,3,4-jk]carbazol-7-yl)oxy]-1-ethanamine; mp 127–128° C.

$^1$H NMR (DMSO-$d_6$) δ 3.4, 4.3, 4.7, 6.0, 6.0, 6.96, 7.04, 7.19, 7.3, 7.4, 7.8, 8.2. Anal. Calcd for $C_{26}H_{25}Cl_1N_2O_6 \cdot 0.25$ ($C_2H_6O_1$): C, 62.85; H, 4.88; N, 5.53; Cl, 7.13. Found: C, 62.6; H, 4.92; N, 5.45. Conversion to the maleic acid salt gave 0.0275 g (7.3%) of 2-[(8-chloro-1-phenyl-1,2-dihydro[1,4]oxazino[2,3,4-jk]carbazol-7-yl)oxy]-1-ethanamine, maleic acid salt; mp 171° C.; $^1$H NMR (CDCl$_3$) δ 2.79, 3.66, 4.39, 4.5, 4.55, 5.38, 6.39, 6.91, 7.15, 7.36, 7.70, 8.17.

Preparation 19A 7-Methyl-3-phenyl-2H-1,4-benzoxazine

To potassium carbonate (63.89 g, 462 mmol) in water (300 mL) and $CH_2Cl_2$ (200 mL) is added 6-amino-m-cresol (10.0 g, 81.2 mmol) and tetra-n-butyl ammonium hydrogensulfate (0.139 g, 0.41 mmol). With vigorous stirring a solution of 2-bromoacetophenone (16.16 g, 81.2 mmol) is added dropwise over a period of 45 min. The mixture is allowed to stir overnight. The layers are then separated and the organic layer is washed with 1N NaOH (500 mL) and water (2×300 mL), dried over magnesium sulfate and concentrated. Column chromatography (400 g silica gel) using ethyl acetate/hexane (20/80) as eluent gave 8.96 g (49%) of 7-methyl-3-phenyl-2H-1,4-benzoxazine.

$^1$H NMR (CDCl$_3$) δ 2.34, 5.06, 6.74, 6.82, 7.32, 7.47, 7.92. Anal. Calcd for $C_{15}H_{13}NO$: C, 80.69; H, 5.87; N, 6.27. Found: C, 80.76; H, 5.88; N, 6.21.

Preparation 19B 7-Methyl-3-phenyl-2H-1,4-benzoxazine

To a slurry of 7-methyl-3-phenyl-2H-1,4-benzoxazine (37.23 g, 167 mmol) in absolute ethanol (200 mL) is added sodium borohydride (12.62 g, 333 mmol). The mixture is refluxed at 95° C. for 1.5 h. The mixture is then concentrated and partitioned between $CH_2Cl_2$ and water. The organic layer is washed twice with water (500 mL), dried over magnesium sulfate and concentrated to dryness. The resulting solid is dried to give 22.53 g (60%) of 7-methyl-3-phenyl-2H-1,4-benzoxazine.

IR (drift) 3349, 3338, 1514, 1456, 1351, 1319, 1296, 1279, 1229, 1154, 1135, 870, 811, 758, 701 cm$^{-1}$; $^1$H NMR (CDCl$_3$) δ 2.25, 3.97, 4.26, 4.47, 6.62, 6.69, 7.41. Anal. Calcd for $C_{15}H_{15}NO$: C, 79.97; H, 6.71; N, 6.22. Found: C, 79.96; H, 6.79; N, 6.20.

Preparation 20 7-Methyl-4-nitroso-3-phenyl-3,4-dihydro-2H-1,4-benzoxazine

To a mixture of 7-methyl-3-phenyl-2H-1,4-benzoxazine (22.5 g, 99.87 mmol) in ethyl ether (300 mL) is added trifluoroacetic acid (7.7 mL, 99.87 mmol). The resulting solution is chilled to 5° C. in an ice bath and n-butyl nitrite (12.26 mL, 99.87 mmol) is added dropwise. The mixture is stirred for 1 h; solids formed during the reaction. The solids are collected by filtration and washed with ether. The filtrates are partitioned between ether and water and the organic layers are washed three times with water (500 mL), dried over magnesium sulfate, and concentrated to dryness. The combined solids gave 23.22 g (97%) of 7-methyl-4-nitroso-3-phenyl-3,4-dihydro-2H-1,4-benzoxazine.

IR (drift) 1499, 1445, 1360, 1326, 1306, 1256, 1232, 1156, 1143, 1134, 1068, 1058, 820, 739, 697 cm$^{-1}$; $^1$H NMR (CDCl$_3$) δ 2.36, 4.21, 4.54, 6.02, 6.87, 6.91, 7.17, 7.26, 8.06; Anal. Calcd for $C_{15}H_{14}N_2O_2$: C, 70.85; H, 5.55; N, 11.02. Found: C, 70.96; H, 5.65; N, 11.01.

Preparation 21 7-Methyl-3-phenyl-2,3-dihydro-4H-1,4-benzoxazin-4-amine

A slurry of lithium aluminum hydride (6.9 g, 183 mmol) in ethyl ether (300 mL) is stirred in an ice bath under an argon atmosphere. A solution of 7-methyl-4-nitroso-3-phenyl-3,4-dihydro-2H-1,4-benzoxazine (23.22 g, 91.3 mmol) in ethyl ether (250 mL) and dry THF (40 mL) is added dropwise over 1.5 h. The mixture is removed from the ice bath and allowed to stir for 18 h. Water (50 mL) is slowly added, forming solids. The solids are collected by filtration and washed with ethyl ether. The resulting filtrates are combined and washed three times with water (400 mL), dried over magnesium sulfate, and concentrated to dryness to give a solid. The solids are slurried in hexane, collected, and dried to give 16.5 g (69%) of 7-methyl-3-phenyl-2,3-dihydro-4H-1,4-benzoxazin-4-amine.

IR (drift) 2912, 1579, 1505, 1455, 1318, 1305, 1243, 1233, 1163, 1050, 892, 835, 804, 759, 702 cm$^{-1}$; $^1$H NMR (CDCl$_3$) δ 2.26, 4.25, 6.65, 6.72, 7.28, 7.37. Anal. Calcd for $C_{15}H_{16}N_2O$: C, 74.97; H, 6.71; N, 11.66. Found: C, 75.11; H, 6.70; N, 11.53.

Preparation 22 5-Methyl-1-phenyl-1,2,9,10-tetrahydro[1,4]oxazino[2,3,4-jk]carbazol-7(8H)-one To a mixture of 7-methyl-3-phenyl-2,3-dihydro-4H-1,4-benzoxazin-4-amine (5.95 g, 24.8 mmol) in toluene (175 mL) is added while stirring 1,3 cyclohexandione (2.86 g, 25.5 mmol). The mixture is heated to 95° C. for 20 min, at which time p-toluenesulfonic acid monohydrate (4.71 g, 24.8 mmol) is added and the temperature is increased to 106° C. for 1 h. The mixture is refluxed for 12 h, then cooled to room temperature and concentrated. The residue is partitioned between $CH_2Cl_2$/1N NaOH. The organic layer is washed with brine, dried over magnesium sulfate and concentrated to dryness. Column chromatography (100 g silica gel) using acetone/hexane (25/75) as eluent gave 4.06 g (51%) of 5-methyl-1-phenyl-1,2,9,10-tetrahydro[1,4]oxazino[2,3,4-jk]carbazol-7(8H)-one; mp 171° C.

IR (drift)2943, 1644, 1640, 1481, 1456, 1397, 1323, 1307, 1265, 1191, 1123, 1017, 836, 763, 704 cm$^{-1}$; $^1$H NMR (CDCl$_3$) δ 2.07, 2.42, 2.47, 2.54, 2.62, 4.45, 4.54, 5.37, 6.63, 7.05, 7.36, 7.6. Anal. Calcd for $C_{21}H_{19}NO_2$: C, 79.47; H, 6.03; N, 4.41. Found: C, 78.72; H, 6.23; N, 5.02.

Preparation 23 5-Methyl-1-phenyl-1,2-dihydro[1,4]oxazino[2,3,4-jk]carbazol-7-ol

To 5-methyl-1-phenyl-1,2,9,10-tetrahydro[1,4]oxazino[2,3,4-jk]carbazol-7(8H)-one (9.0 g, 28.4 mmol) in ethyl acetate/acetonitrile (150 mL/50 mL) is added trifluoroacetic acid (4 mL) and anhydrous cupric chloride (9.7 g, 56.7 mmol). The mixture is heated to reflux at 90° C. for 7 h. The mixture is poured into methylene chloride (500 mL) and filtered to remove inorganic solids. The filtrates are washed with saturated potassium carbonate solution followed by water, dried over magnesium sulfate and concentrated. The residue is dissolved in DMF (20 mL) to which is added lithium bromide (4.2 g, 56.7 mmol) and lithium carbonate (4.9 g, 56.7 mmol). The mixture is heated at 119° C. for 5 h, then partitioned between water and CH$_2$Cl$_2$. The organic layer is washed twice with brine (30 mL). Column chromatography (200 g silica gel) using EtOAc/hexanes (20/80) as eluent gave 1.3 g (14.5%) of 5-methyl-1-phenyl-1,2-dihydro[1,4]oxazino[2,3,4-jk]carbazol-7-ol.

IR (drift) 3407, 1489, 1463, 1446, 1382, 1332, 1296, 1275, 1132, 1117, 1024, 841, 752, 744, 704 cm$^{-1}$; $^1$H NMR (CDCl$_3$) δ 2.55, 4.47, 4.58, 6.37, 6.53, 6.81, 7.03, 7.17, 7.34, 7.63. Anal. Calcd for $C_{21}H_{17}NO_2$: C, 79.98; H, 5.43; N, 4.44. Found: C, 79.22; H, 5.50; N, 4.34.

Preparation 24 2-[(5-Methyl-1-phenyl-1,2-dihydro[1,4]oxazino[2,3,4-jk]carbazol-7-yl)oxy]acetonitrile To a mixture of 5-methyl-1-phenyl-1,2-dihydro[1,4]oxazino[2,3,4-jk]carbazol-7-ol (1.3 g, 4.12 mmol) in DMF (15 mL) is added potassium carbonate (2.8 g, 20.6 mmol) and bromoacetonitrile (1.4 mL, 20.6 mmol). The mixture is heated at 85° C. for 1.5 h. The mixture is cooled and partitioned between water and CH$_2$Cl$_2$. The organic layer is washed twice with water (200 mL), dried over magnesium sulfate and concentrated. Column chromatography (100 g silica gel) using ethyl acetate/hexanes (20/80) eluent gave 0.665 g (46%) of 2-[(5-methyl-1-phenyl-1,2-dihydro[1,4]oxazino[2,3,4-jk]carbazol-7-yl)oxy]acetonitrile.

IR(drift) 1594, 1488, 1465, 1448, 1333, 1313, 1274, 1259, 1238, 1177, 1162, 1139, 1025, 749, 701 cm$^{-1}$; $^1$H NMR (CDCl$_3$) δ 4.49, 4.61, 5.03, 5.53, 6.54, 6.70, 6.98, 7.17, 7.36, 7.82. Anal. Calcd for $C_{23}H_{18}N_2O_2$: C, 77.95; H, 5.12; N, 7.90. Found: C, 77.34; H, 5.19; N, 7.61.

Example 10

2-[(5-Methyl-1-phenyl-1,2-dihydro[1,4]oxazino[2,3,4-jk]carbazol-7-yl)oxy]-1-ethanamine

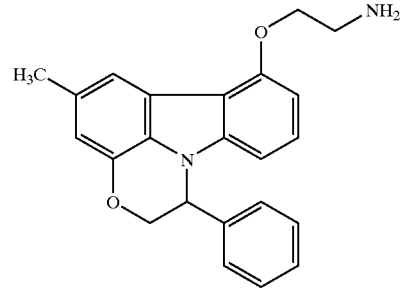

To a mixture of 2-[(5-methyl-1-phenyl-1,2-dihydro[1,4]oxazino[2,3,4-jk]carbazol-7-yl)oxy]acetonitrile (0.66 g, 1.86 mmol) in dry THF (120 mL) is added borane-methylsulfide complex (0.53 mL, 5.6 mmol). The mixture is refluxed at 85° C. for 18 h. The mixture is removed from heat and methanol is slowly added until gas evolution ceased. The solvents are removed under vacuum and methanol (5 mL) is added and again removed. The residue is dissolved in CH$_2$Cl$_2$/CH$_3$OH (1:2 15 mL). Conc. HCl (2 mL) is added and the mixture heated at 65° C. for 1 h. The mixture is removed from heat and neutralized with aqueous potassium carbonate then partitioned between water and CH$_2$Cl$_2$. The organic layer is washed with water, dried over magnesium sulfate, and concentrated. Column chromatography (70 g silica gel) using CH$_3$OH/CH$_2$Cl$_2$ (4:96) as eluent gave 0.444 g (67%) of 2-[(5-methyl-1-phenyl-1,2-dihydro[1,4]oxazino[2,3,4-jk]carbazol-7-yl)oxy]-1-ethanamine.

IR (drift) 1593, 1576, 1487, 1448, 1335, 1313, 1261, 1162, 1138, 1129, 1022, 838, 779, 750, 702 cm$^{-1}$; $^1$H NMR (CDCl$_3$) δ 3.30, 4.25, 4.46, 4.57, 5.48, 6.42, 6.59, 6.93, 7.15, 7.32, 7.83. Anal. Calcd for $C_{23}H_{22}N_2O_2$: C, 77.07; H, 6.19; N, 7.82. Found: C, 76.62; H, 6.29; N, 7.68.

Preparation 25 N-{2-[(5-Methyl-1-phenyl-1,2-dihydro[1,4]oxazino[2,3,4-jk]carbazol-7-yl)oxy]ethyl}acetamide

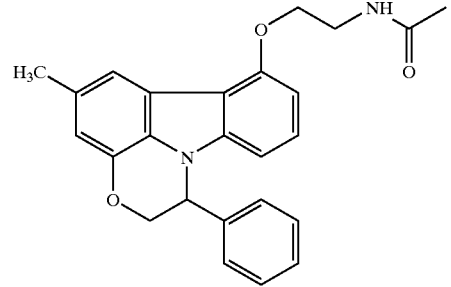

To a mixture of 2-[(5-methyl-1-phenyl-1,2-dihydro[1,4]oxazino[2,3,4-jk]carbazol-7-yl)oxy]-1-ethanamine (0.0.442 g, 1.23 mmol) in DMF (10 mL) is added acetic anhydride (0.126 g, 1.23 mmol) and DMAP (0.08 g, 0.66 mmol). The mixture is heated at 95° C. for 1 h and then partitioned between water and ether after cooling. The organic layer is washed three times with water (60 mL), dried over magnesium sulfate and concentrated to give 0.49 g (99%) of N-{2-[(5-methyl-1-phenyl-1,2-dihydro[1,4]oxazino[2,3,4-jk]carbazol-7-yl)oxy]ethyl}acetamide.

IR (drift) 1662, 1655, 1646, 1593, 1574, 1551, 1506, 1487, 1448, 1335, 1312, 1258, 1138, 750, 703 cm$^{-1}$; $^1$H NMR (CDCl$_3$) δ 2.03, 3.87, 4.32, 4.50, 4.61, 5.52, 6.46, 6.62, 6.97, 7.18, 7.33, 7.79. Anal. Calcd for C$_{25}$H$_{24}$N$_2$O$_3$: C, 74.98; H, 6.04; N, 6.99. Found: C, 74.56; H, 6.06; N, 6.80.

Example 11

N-Ethyl-2-[(5-methyl-1-phenyl-1,2-dihydro[1,4]oxazino[2,3,4-jk]carbazol-7-yl)oxy]-1-ethanamine and its Maleic Acid Salt

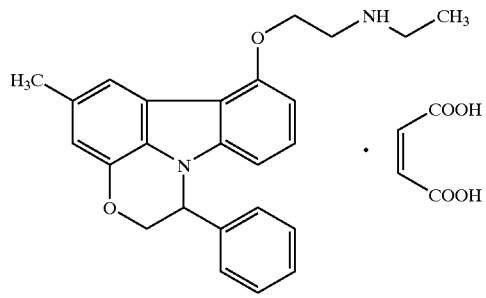

To a mixture of N-{2-[(5-methyl-1-phenyl-1,2-dihydro[1,4]oxazino[2,3,4-jk]carbazol-7-yl)oxy]ethyl}acetamide (0.212 g, 0.53 mmol) in THF (10 mL) is added borane-methylsulfide complex (0.15 mL, 1.6 mmol). The mixture is refluxed at 85° C. for 16 hours. After cooling, methanol is slowly added until gas evolution ceased. The solvents are removed under vacuum and methanol (5 mL) is added then removed. The residue is dissolved in CH$_2$Cl$_2$/CH$_3$OH (1:5, 15 mL). Conc. HCl is added and the mixture is heated at 65° C. for 1 h. The mixture is removed from heat, neutralized with aqueous potassium carbonate and then partitioned between water and CH$_2$Cl$_2$ The organic layer is washed with water, dried over magnesium sulfate, and concentrated. Column chromatography (70 g silica gel) using CH$_3$OH/CH$_2$Cl$_2$ (5:95) as eluent gave 0.148 g (70%) of N-ethyl-2-[(5-methyl-1-phenyl-1,2-dihydro[1,4]oxazino[2,3,4-jk]carbazol-7-yl)oxy]-1-ethanamine (TLC: MeOH/CH$_2$Cl$_2$, 5/95, R$_f$=0.38); conversion to the maleic acid salt and recrystallizing from absolute ethanol gave 0.0223 g of N-ethyl-2-[(5-methyl-1-phenyl-1,2-dihydro[1,4]oxazino[2,3,4-jk]carbazol-7-yl)oxy]-1-ethanamine, maleic acid salt.

IR (drift) 1593, 1573, 1485, 1457, 1448, 1351, 1337, 1318, 1257, 1140, 1130, 1031, 866, 748, 721 cm$^{-1}$; $^1$H NMR (CDCl$_3$) δ 1.42, 2.5, 3.3, 3.59, 4.43, 4.53, 5.43, 6.41, 6.51, 6.79, 7.09, 7.31, 7.55. Water (KF): 0.24%. Anal. Calcd for C$_{25}$H$_{26}$N$_2$O$_2$.C$_4$H$_4$O$_4$.0.24% water: C, 69.14; H, 6.03; N, 5.56. Found: C, 68.84; H, 6.12; N,5.47.

Preparation 26 7-(2-chloroethoxy)-1-phenyl-1,2-dihydro[1,4]oxazino[2,3,4-jk]carbazole To a mixture of 1-phenyl-1,2-dihydro[1,4]oxazino[2,3,4-jk]carbazol-7-ol (3.0 g 9.96 mmol) and potassium carbonate (6.9 g, 50 mmol) in dry DMF (70 mL) is added 1-bromo-2-chloroethane (4.0 mL, 50 mmol). The mixture is heated to 85° C. for 8.25 h. The mixture is then partitioned between water and Et$_2$O. The organic layer is separated and washed three times with water (100 mL), dried over anhydrous sodium sulfate, filtered and concentrated. Column chromatography (200 mL silica) using CH$_2$Cl$_2$/hexanes (1/1) as eluent gave 3.4 g (94%) of 7-(2-chloroethoxy)-1-phenyl-1,2-dihydro[1,4]oxazino[2,3,4-jk]carbazole.

IR (drift) 1637, 1585, 1496, 1450, 1431, 1323, 1311, 1265, 1239, 1151, 1041, 790, 738, 718, 700 cm$^{-1}$; $^1$H NMR (CDCl$_3$) δ 4.04, 4.55, 4.64, 5.5, 6.5, 6.6, 7.0, 7.2, 7.4, 7.9.

Example 12 tert-Butyl 4-{2-[(1-phenyl-1,2-dihydro[1,4]oxazino[2,3,4-jk]carbazol-7-yl)oxy]ethyl}-1-piperazinecarboxylate

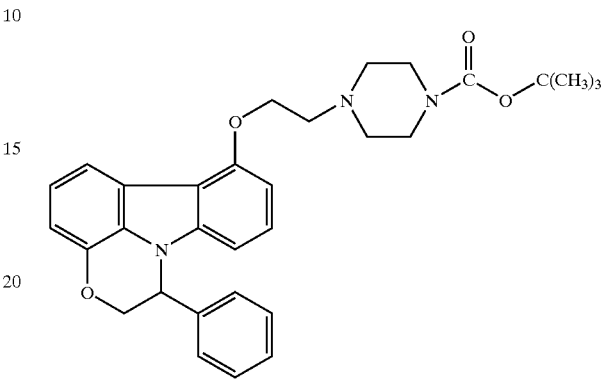

To a mixture of 7-(2-chloroethoxy)-1-phenyl-1,2-dihydro[1,4]oxazino[2,3,4-jk]carbazole (0.453 g, 1.24 mmol) in dry DMF (6 mL) is added tert-butyl-1-piperazinecarboxylate (0.232 g, 1.24 mmol), sodium iodide (0.018 g, 0.124 mmol), and potassium carbonate (0.342 g, 2.48 mmol). The mixture is heated at 85° C. for 20 h. The mixture is then cooled and partitioned between Et$_2$O and water. The organic layer is washed twice with water (200 mL), dried over anhydrous sodium sulfate and concentrated. Column chromatography (50 mL silica) using CH$_2$Cl$_2$/CH$_3$OH (98/2) yielded 0.487 g (76%) of tert-butyl 4-{2-[(1-phenyl-1,2-dihydro[1,4]oxazino[2,3,4-jk]carbazol-7-yl)oxy]ethyl}-1-peperazinecarboxylate; mp 72° C.;.

IR (drift) 1693, 1585, 1496, 1452, 1428, 1365, 1310, 1263, 1241, 1175, 1159, 1151, 1129, 790, 738 cm$^{-1}$; $^1$H NMR (CDCl$_3$) δ 1.5, 2.7, 3.1, 3.5, 4.4, 4.5, 4.6, 5.5, 6.5, 6.6, 7.0, 7.2, 7.4, 7.9. Anal. Calcd for C$_{31}$H$_{35}$N$_3$O$_4$: C, 72.49; H, 6.87; N, 8.18. Found: C, 72.15; H, 6.90; N, 8.14.

Example 13

1-Phenyl-1,2-dihydro[1,4]oxazino[2,3,4-jk]carbazol-7-yl 2-(1-piperazinyl)ethyl Ether

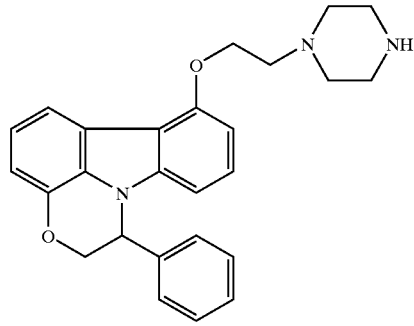

To a mixture of tert-butyl 4-{2-[(1-phenyl-1,2-dihydro[1,4]oxazino[2,3,4-jk]carbazol-7-yl)oxy]ethyl}-1- piperazinecarboxylate (0.406 g, 0.79 mmol) in $CH_2Cl_2$ (2 mL) is added trifluoroacetic acid (2 mL). The mixture is stirred at room temperature for 1 h then partitioned between $CH_2Cl_2$ and water. The organic layer is washed with saturated potassium carbonate, dried over anhydrous sodium sulfate and concentrated. Column chromatography (50 mL silica) using $CH_3OH/CH_2Cl_2$ (8/92) with 2 drops per 100 mL of $NH_4OH$ gave 0.133 g (35%) of 1-phenyl-1,2-dihydro [1,4]oxazino[2,3,4-jk]carbazol-7-yl 2-(1-piperazinyl)ethyl ether; mp 72° C.

IR (drift) 2936, 2817, 1585, 1497, 1451, 1431, 1322, 1310, 1265, 1240, 1151, 790, 738, 718, 700 cm$^{-1}$; $^1$H NMR (CDCl$_3$) δ 2.8, 3.0, 4.4, 4.5, 4.6, 5.5, 6.4, 6.6, 7.0, 7.2, 7.4, 7.9. Water (KF), 1.64%. Anal. Calcd for $C_{26}H_{27}N_3O_2$·1.64% $H_2O$: C, 74.28; H, 6.66; N, 9.99. Found: C, 73.94; H, 6.77; N, 9.82.

Example 14

2-(4-Methyl-1-piperazinyl)ethyl 1-phenyl-1,2-ihydro [1,4]oxazino [2,3,4-jk]carbazol-7-yl Ether

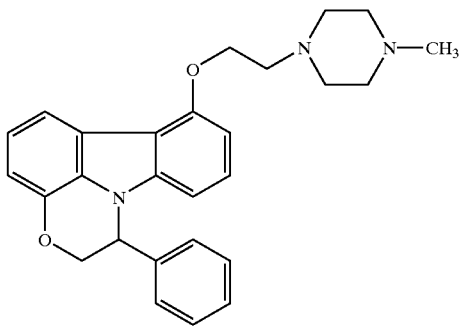

To a mixture of 7-(2-chloroethoxy)-1-phenyl-1,2-dihydro [1,4]oxazino[2,3,4-jk]carbazole (0.412 g, 1.13 mmol) in dry DMF (10 mL) is added N-methyl piperazine (0.125 mL, 1.13 mmol), sodium iodide (0.17 g, 1.13 mmol), and potassium carbonate (0.312 g, 2.26 mmol). The mixture is heated at 85° C. for 20 h. The mixture is then cooled and partitioned between water and $CH_2Cl_2$. The organic layer is separated and washed twice with water (200 mL), dried over anhydrous sodium sulfate and concentrated. Column chromatography (50 mL silica) using $CH_3OH/CH_2Cl_2$ (8/92) with 2 drops per 100 mL of $NH_4OH$ gave 0.156 g (32%) of 2-(4-methyl-1-piperazinyl)ethyl 1-phenyl-1,2-dihydro[1,4] oxazino[2,3,4-jk]carbazol-7-yl ether; mp 57° C.

IR (drift) 2934, 2793, 1585, 1496, 1451, 1323, 1311, 1283, 1264, 1240, 1177, 1167, 1150, 790, 737 cm$^{-1}$; $^1$H NMR (CDCl$_3$) δ 2.35, 2.6, 2.8, 3.1, 4.4, 4.5, 4.6, 5.5, 6.4, 6.6, 7.0, 7.2, 7.4, 7.9. Water (KF), 1.33%. Anal. Calcd for $C_{27}H_{29}N_3O_2$·1.33% $H_2O$: C, 74.84; H, 6.89; N, 9.70. Found: C, 74.90; H, 6.93; N, 9.58.

Example 15

2-(4-Morpholinyl)ethyl 1-phenyl-1,2-dihydro[1,4] oxazino[2,3,4-jk]carbazol-7-yl Ether

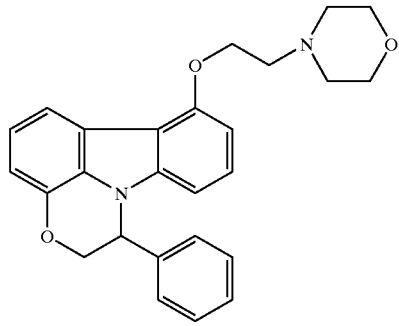

To a mixture of 7-(2-chloroethoxy)-1-phenyl-1,2-dihydro [1,4]oxazino[2,3,4-jk]carbazole (0.278 g, 0.764 mmol) in dry DMF (10 mL) is added morpholine (0.133 g, 1.53 mmol), sodium iodide (0.114 g, 0.764 mmol), and potassium carbonate (0.211 g, 1.53 mmol). The mixture is heated to 100° C. for 6 h. The mixture is removed from heat and stirred at room temperature for three days. The mixture is then partitioned between water and $Et_2O$. The layers are separated and the organic layer is washed twice with water (50 mL) and then dried over anhydrous sodium sulfate and concentrated. Column chromatography (50 mL silica) using $CH_2Cl_2$/acetone/hexanes (7:2:1) gave 0.192 g (61%) of 2-(4-morpholinyl)ethyl 1-phenyl-1,2-dihydro[1,4]oxazino [2,3,4-jk]carbazol-7-yl ether.

IR (drift) 1585, 1497, 1451, 1350, 1323, 1311, 1265, 1240, 1151, 1116, 1040, 790, 738, 718, 699 cm$^{-1}$; $^1$H NMR (CDCl$_3$) δ 2.7, 3.1, 3.8, 4.4, 4.5, 4.6, 5.5, 6.5, 6.6, 7.0, 7.2, 7.4, 7.9. Anal. Calcd for $C_{26}H_{26}N_2O_3$: C, 75.34; H, 6.32; N, 6.76. Found: C, 74.94; H, 6.31; N, 6.69.

Example 16

1-Phenyl-1,2-dihydro[1,4]oxazino[2,3,4-jk]carbazol-7-yl 2-(1-piperidinyl)ethyl Ether and its Methanesulfonic Acid Salt

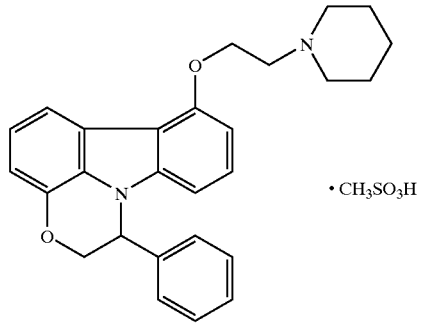

To a mixture of 7-(2-chloroethoxy)-1-phenyl-1,2-dihydro [1,4]oxazino[2,3,4-jk]carbazole (0.28 g, 0.769 mmol) in dry DMF (6 mL) is added sodium iodide (0.09 g, 0.6 mmol), potassium carbonate (0.207 g, 1.5 mmol), and piperidine (0.13 g, 1.5 mmol). The mixture is heated at 70° C. for 6 h and then at room temperature for 18 h. The mixture is then partitioned between water and ether. The ether layer is washed three times with water (80 mL). The organic layer is dried over sodium sulfate and concentrated. Column chromatography (50 mL) silica gel using 1% methanol in $CH_2Cl_2$ as eluent gave 1-phenyl-1,2-dihydro[1,4]oxazino[2,3,4-jk]carbazol-7-yl 2-(1-piperidinyl)ethyl ether (TLC: acetone/hexane, 20/80, $R_f$=0.42) which is converted to the methanesulfonate salt to give 0.134 g (34%) of 1-phenyl-1,2-dihydro[1,4]oxazino[2,3,4-jk]carbazol-7-yl 2-(1-piperidinyl)ethyl ether.

IR (drift) 1585, 1497, 1451, 1323, 1311, 1260, 1239, 1225, 1198, 1179, 1151, 1038, 790, 768, 740 cm$^{-1}$; $^1$H NMR (CDCl$_3$) δ 1.7, 2.0, 2.9, 3.0, 3.7, 3.8, 4.5, 4.6, 4.8, 5.5, 6.5, 6.7, 7.0, 7.2, 7.4, 7.7. Anal. Calcd for $C_{27}H_{28}N_2O_2 \cdot CH_4O_3S \cdot 2.92\%$ $H_2O$: C, 64.19; H, 6.48; N, 5.35;. Found: C, 64.01; H, 6.52; N, 5.29.

Example 17

2-({2-[(1-Phenyl-1,2-dihydro[1,4]oxazino[2,3,4-jk]carbazol-7-yl)oxy]ethyl}amino)-1-ethanol

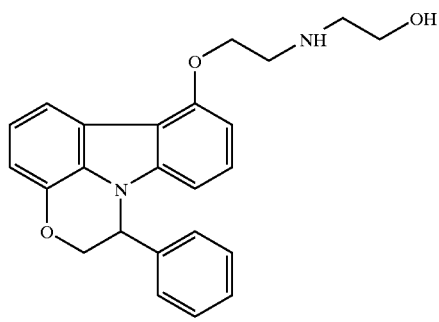

To a mixture of 7-(2-chloroethoxy)-1-phenyl-1,2-dihydro[1,4]oxazino[2,3,4-jk]carbazole (0.273 g, 0.751 mmol) in dry DMF (10 mL) is added sodium iodide (0.113 g, 0.751 mmol), potassium carbonate (0.207 g, 1.5 mmol), and ethanolamine (0.046 g, 0.751 mmol). The mixture is heated at 85° C. for 17 h. The temperature is then increased to 90° C. and the mixture is allowed to stir for another 5 h. The mixture is then cooled to room temperature and partitioned between water and ether. The organic layer is washed twice with water (50 mL), dried over anhydrous sodium sulfate and concentrated. Column chromatography (50 mL silica gel) using 5% methanol in $CH_2Cl_2$ gave 0.123 g (42%) of 2-({2-[(1-phenyl-1,2-dihydro[1,4]oxazino[2,3,4-jk]carbazol-7-yl)oxy]ethyl}amino)-1-ethanol.

IR (drift) 1584, 1495, 1451, 1351, 1324, 1310, 1267, 1242, 1153, 1086, 1041, 791, 742, 720, 702 cm$^{-1}$; $^1$H NMR (CDCl$_3$) δ 3.0, 3.3, 3.7, 4.4, 4.5, 4.6, 5.5, 6.5, 6.7, 7.0, 7.2, 7.4, 7.8. Water (KF), 0.96%. Anal. Calcd for $C_{24}H_{24}N_2O_3 \cdot 0.96\%$ $H_2O$: C, 73.49; H, 6.27; N, 7.14. Found: C, 73.61; H, 6.32; N, 7.10.

Example 18

N,N-dimethyl-2-[(1-phenyl-1,2-dihydro[1,4]oxazino[2,3,4-jk]carbazol-7-yl)oxy]-1-ethanamine

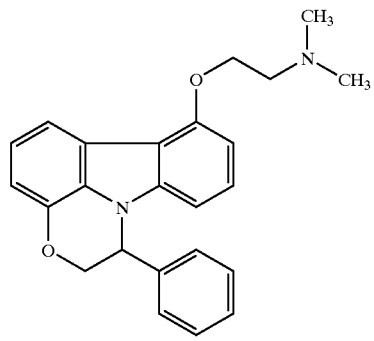

To a mixture of 2-chloroethyl 1-phenyl-1,2-dihydro[1,4]oxazino[2,3,4-jk]carbazol-7-yl ether (0.248 g, 0.68 mmol) in dry DMF (10 mL) is added potassium carbonate (0.376 g, 2.7 mmol), sodium iodide (0.101 g, 0.68 mmol), and 2M dimethylamine in THF (0.68 mL, 1.36 mmol). The mixture is stirred for 48 h at room temperature. The mixture is then partitioned between water and $Et_2O$. The organic layer is washed three times with water (100 mL), dried over anhydrous sodium sulfate and concentrated. Column chromatography (50 mL silica) using $CH_2Cl_2$ followed by $CH_3OH/CH_2Cl_2$ (95/5) as eluent and then drying of the appropriate fractions under house vacuum gave 0.020 g (8%) of N,N-dimethyl-2-[(1-phenyl-1,2-dihydro[1,4]oxazino[2,3,4-jk]carbazol-7-yl)oxy]-1-ethanamine; mp 117–118° C.

$^1$H NMR (CDCl$_3$) δ 2.82, 3.43, 4.47, 4.60, 4.49, 6.45, 6.61, 6.94, 7.11, 7.32, 7.75.

Example 19

2-[(5-Methyl-1-phenyl-1,2-dihydro[1,4]oxazino[2,3,4-jk]carbazol-7-yl)oxy]-1-ethanamine

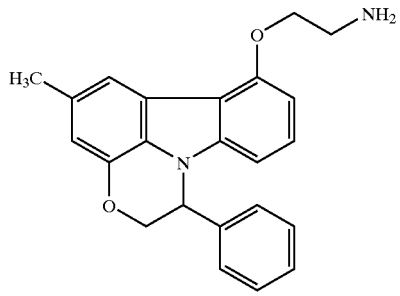

To a mixture of 2-[(5-methyl-1-phenyl-1,2-dihydro[1,4]oxazino[2,3,4-jk]carbazol-7-yl)oxy]acetonitrile (0.66 g, 1.86 mmol) in dry THF (120 mL) is added borane-methylsulfide complex (0.53 mL, 5.6 mmol). The mixture is refluxed at 85° C. for 18 h. The mixture is removed from heat and methanol is slowly added until gas evolution ceased. The solvents are removed under vacuum and methanol (5 mL) is added and again removed. The residue is dissolved in CH₂Cl₂/CH₃OH (1:2 15 mL). Conc. HCl (2 mL) is added and the mixture heated at 65° C. for 1 h. The mixture is removed from heat and neutralized with aqueous potassium carbonate then partitioned between water and CH₂Cl₂. The organic layer is washed with water, dried over magnesium sulfate, and concentrated. Column chromatography (70 g silica gel) using CH₃OH/CH₂Cl₂ (4:96) as eluent gave 0.444 g (67%) of the title compound;

IR (drift) 1593, 1576, 1487, 1448, 1335, 1313, 1261, 1162, 1138, 1129, 1022, 838, 779, 750, 702 cm$^{-1}$; $^1$H NMR (CDCl₃) δ 3.30, 4.25, 4.46, 4.57, 5.48, 6.42, 6.59, 6.93, 7.15, 7.32, 7.83. Anal. Calcd for C₂₃H₂₂N₂O₂: C, 77.07; H, 6.19; N, 7.82. Found: C, 76.62; H, 6.29; N, 7.68.

Preparation 27 4-Chlorobutyl 1-phenyl-1,2-dihydro[1,4]oxazino[2,3,4-jk]carbazol-7-yl Ether To a mixture of 1-phenyl-1,2-dihydro[1,4]oxazino[2,3,4-jk]carbazol-7-ol (0.5 g, 1.66 mmol) in dry DMF (5 mL) is added potassium carbonate (1.15 g, 8.3 mmol) and 1-bromo-4-chlorobutane (1.4 g, 8.3 mmol). The mixture is heated at 85° C., under argon, for 4 h. The mixture is then cooled to room temperature and water (50 mL) is added. The mixture is transferred to a separatory funnel and partitioned between water and ether. The ether layer is washed with water (50 mL) then dried over anhydrous sodium sulfate. The ether filtrates are then concentrated. Column chromatography (50 mL silica) using hexanes followed by hexanes/methylene chloride (1:1) gave 0.373 g (57%) of the title compound.

$^1$H NMR (CDCl₃) δ 2.16, 3.58, 3.71, 4.28, 4.50, 4.60, 5.52, 6.43, 6.62, 6.95, 7.16, 7.34, 7.84.

Example 20

N,N-Diethyl-N-{4-[(1-phenyl-1,2-dihydro[1,4]oxazino[2,3,4-jk]carbazol-7-yl)oxy]butyl}amine

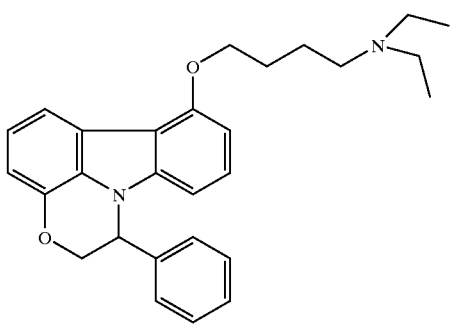

To a mixture of 4-chlorobutyl 1-phenyl-1,2-dihydro[1,4]oxazino[2,3,4-jk]carbazol-7-yl ether (0.36 g, 0.9 mmol) in dry DMF (10 mL) is added potassium carbonate (0.63 g, 4.6 mmol), diethylamine (0.48 mL, 4.6 mmol), and sodium iodide (0.135 g, 0.9 mmol). The mixture is heated at 50° C. for 20 h. The mixture is then cooled to room temperature and partitioned between water and ether. The ether layer is washed twice with water (50 mL) then dried over anhydrous sodium sulfate and concentrated. Column chromatography (60 mL silica) using 5% methanol in methylene chloride as eluent gave 0.127 g (33%) of the title compound.

IR (liq.) 2967, 2933, 1587, 1496, 1458, 1451, 1431, 1323, 1311, 1264, 1239, 1152, 1042, 790, 737 cm$^{-1}$. $^1$H NMR (CDCl₃) δ 1.11, 1.87, 1.99, 2.68, 4.24, 4.50, 4.60, 5.51, 6.42, 6.62, 6.94, 7.17, 7.34, 7.85; Anal. Calcd for C₂₈H₃₂N₂O₂: C, 78.47; H, 7.53; N, 6.54. Found: C, 78.27; H, 7.68; N, 6.47.

Preparation 28 3-Chloropropyl 1-phenyl-1,2-dihydro[1,4]oxazino[2,3,4-jk]carbazol-7-yl Ether To a mixture of 1-phenyl-1,2-dihydro[1,4]oxazino[2,3,4-jk]carbazol-7-ol (0.82 g, 2.7 mmol) in dry DMF (12 mL) is added 1-bromo-3-chloropropane (1.28 g, 8.1 mmol) and potassium carbonate (1.12 g, 8.1 mmol). The mixture is heated at 80° C. for 6 h. The mixture is then stirred at room temperature for 18 h followed by another 6 h at 80° C. The mixture is partitioned between water and CH₂Cl₂. The organic layer is washed 3 times with water (100 mL). The organic layer is then dried over anhydrous sodium sulfate and concentrated. Column chromatography (60 mL silica) using hexanes/CH₂Cl₂ (1:1) as eluent gave an oil which is rechromatographed (60 mL silica) using hexanes/CH₂Cl₂ (60/40) as eluent gave 0.454 g (44%) of the title compound.

IR (drift) 1585, 1497, 1451, 1349, 1323, 1311, 1263, 1239, 1178, 1150, 1040, 790, 737, 718, 699 cm$^{-1}$. $^1$H NMR (CDCl3) δ 2.44, 3.54, 3.90, 4.29, 4.39, 4.5, 4.6, 5.5, 6.4 6.65, 6.95, 7.16, 7.34, 7.79; Anal. Calcd for C₂₃H₂₀ClNO₂: C, 73.11; H, 5.34; N, 3.71; Cl, 9.38. Found: C, 70.92; H, 5.32; N, 3.55.

Example 21

N,N-Diethyl-N-{3-[(1-phenyl-1,2-dihydro[1,4]oxazino[2,3,4-jk]carbazol-7-yl)oxy]propyl}amine

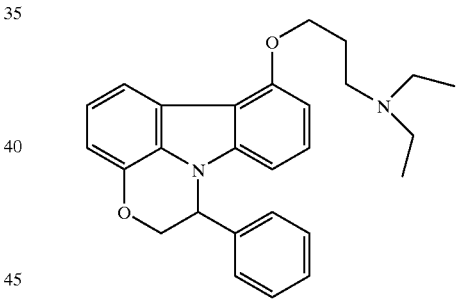

To a mixture of 3-chloropropyl 1-phenyl-1,2-dihydro[1,4]oxazino[2,3,4-jk]carbazol-7-yl ether (0.45 g, 1.2 mmol) in dry DMF (10 mL) is added diethylamine (1.2 mL, 12 mmol) and sodium iodide (0.18 g, 1.2 mmol). The mixture is heated at 50° C. overnight. The mixture is partitioned between water and CH₂Cl₂. The layers are separated and the organic layer washed with brine (50 mL) followed by water (100 mL). The organic layer is dried over anhydrous sodium sulfate, filtered and concentrated. Column chromatography with silica gel (60 mL) using CH₃OH/CH₂Cl₂ (3/97) as eluent gave 0.216 g (43%) of the title compound.

IR (liq.) 2968, 1587, 1578, 1496, 1459, 1451, 1431, 1324, 1312, 1265, 1240, 1179, 1152, 791, 738 cm$^{-1}$. $^1$H NMR (CDCl₃) δ 1.12, 2.18, 2.66, 2.85, 4.25, 4.4), 4.), 5.51, 6.4), 6.63, 6.94, 7.16, 7.32, 7.86; Anal. Calcd for C₂₇H₃₀N₂O₂+ 0.27% H2O: C, 78.02; H, 7.30; N, 6.74. Found: C, 77.41; H, 7.34; N, 6.70.

Preparation 29 2-Chloroethyl (1R)-1-phenyl-1,2-dihydro[1,4]oxazino[2,3,4-jk]carbazol-7-yl Ether To a mixture of (1R)-1-phenyl-1,2-dihydro[1,4]oxazino[2,3,4-jk]carbazol-7-ol (3.67 g, 12.19 mmol) in DMF (90 mL) is added potassium carbonate (8.4 g, 60.9 mmol) and 1-bromo-2-chloroethane (5.0 mL, 60.9 mmol). The mixture is heated to 85° C. for 24 h. The temperature is then increased to 95° C. and heated for 4 h. Mechanical stirring is employed and the reaction heated an additional 1.5 h. The mixture is then partitioned between water and Et$_2$O. The layers are separated and the organic layer washed with water (100 mL). The organic layer is dried over anhydrous sodium sulfate, filtered and concentrated. Column chromatography with silica gel using hexane/CH$_2$Cl$_2$ (60/40) gave 2.4 g (54%) of the title compound.

IR (drift) 1637, 1585, 1497, 1450, 1431, 1323, 1311, 1265, 1239, 1151, 1040, 790, 738, 718, 700 cm$^{-1}$. $[\alpha]^{25}_D$=−86° (c 0.85, methylene chloride). $^1$H NMR (CDCl$_3$) δ 3.85, 4.02, 4.5, 4.6, 5.51, 6.45, 6.60, 6.96, 7.16, 7.34, 7.91; Anal. Calcd for C$_{22}$H$_{18}$ClNO$_2$: C, 72.62; H, 4.99; N, 3.85; Cl, 9.74. Found: C, 69.28; H, 4.95; N, 3.55

Example 22

[(2-{[(1R)-1-Phenyl-1,2-dihydro[1,4]oxazino[2,3,4-jk]carbazol-7-yl]oxy}ethyl)amino]ethanol

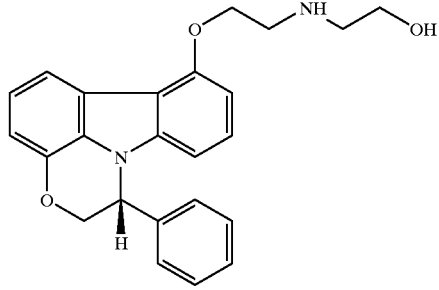

To a mixture of 2-chloroethyl (1R)-1-phenyl-1,2-dihydro[1,4]oxazino[2,3,4-jk]carbazol-7-yl ether in DMF (20 mL) is added sodium iodide (1.0 g, 6.7 mmol), potassium carbonate (2.0 g, 14.5 mmol), and ethanolamine (0.42 mL, 7.0 mmol). The mixture is heated to 85° C. for 18 h. The mixture then is partitioned between water and CH$_2$Cl$_2$. The layers are separated and the organic layer washed twice with water (200 mL). The organic layer is dried over anhydrous sodium sulfate, filtered and concentrated. Column chromatography with silica gel (60 mL) using CH$_3$OH/CH$_2$Cl$_2$ (2/98) and then rechromatographed with CH$_3$OH/CH$_2$Cl$_2$/NH$_4$OH (4/96/0.1) gave 0.62 g (24%) of the title compound.

IR (drift) 1585, 1496, 1451, 1348, 1323, 1311, 1265, 1239, 1151, 1070, 1041, 790, 738, 718, 699 cm$^{-1}$. % Water (KF): 0.73. $[\alpha]^{25}_D$=−78° (c 0.77, methylene chloride). 1H NMR (CDCl3) δ 2.97, 3.24, 3.71, 4.33, 4.49, 4.60, 5.51, 6.44, 6.63, 6.95, 7.16, 7.33, 7.80; Anal. Calcd for C$_{24}$H$_{24}$N$_2$O$_3$ with 0.73% H$_2$O: C, 74.21; H, 6.23; N, 7.21. Found: C, 73.51; H, 6.47; N, 7.04.

CHART A

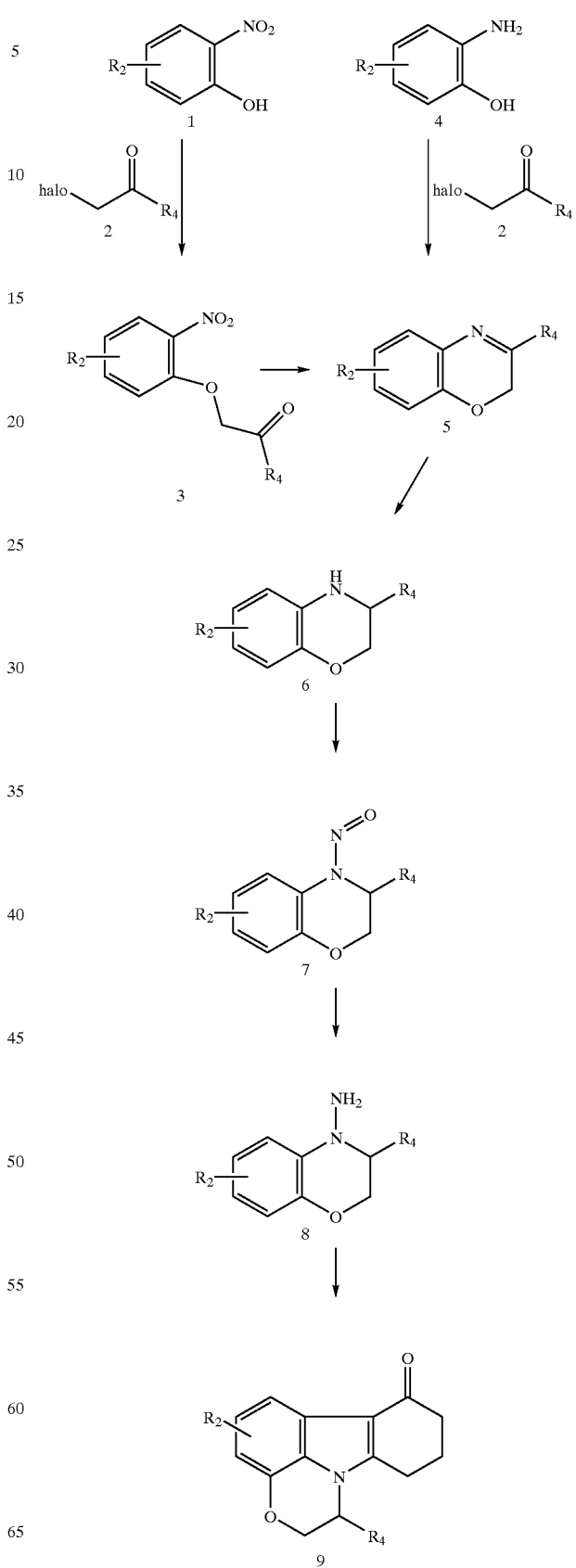

CHART B
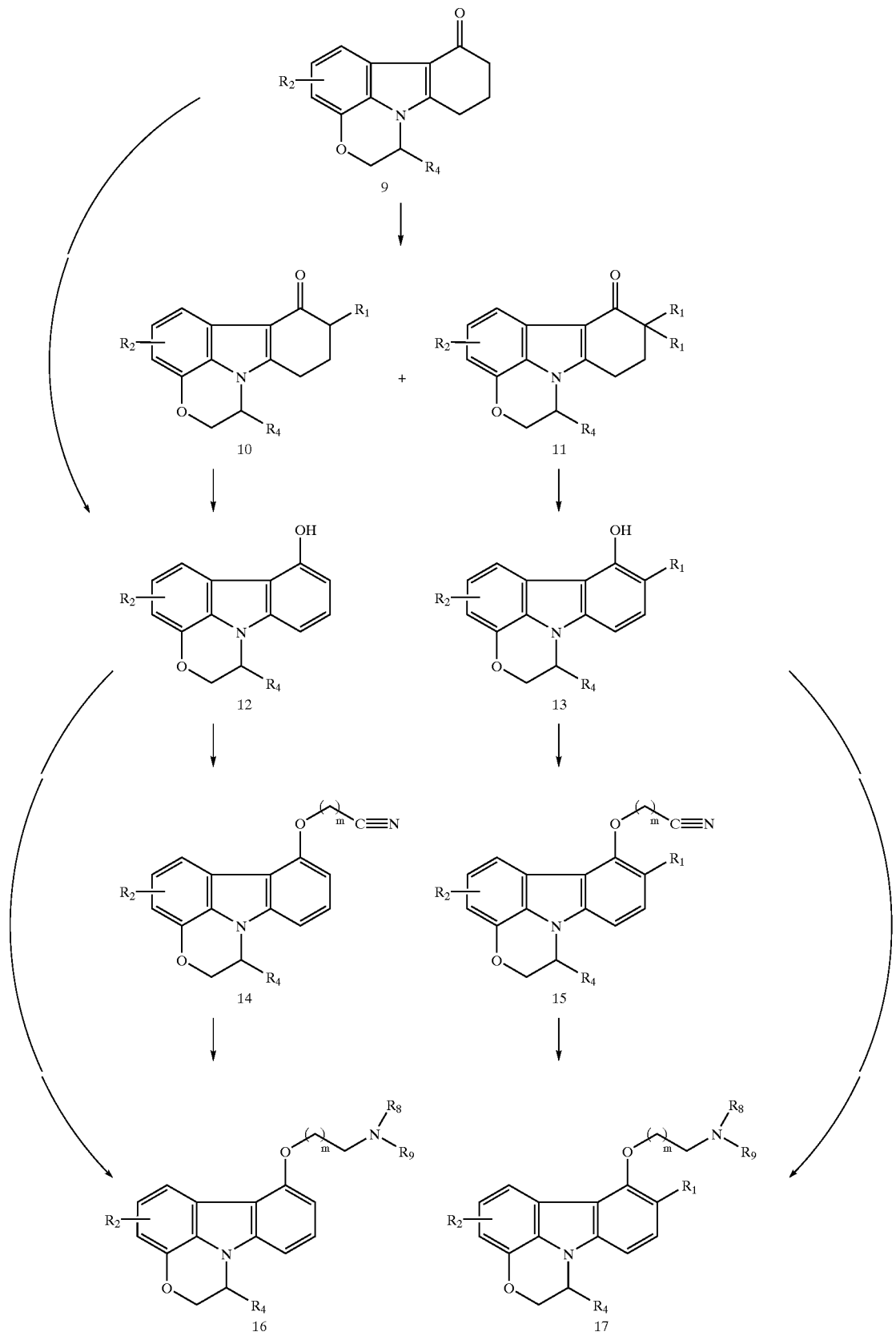

CHART C
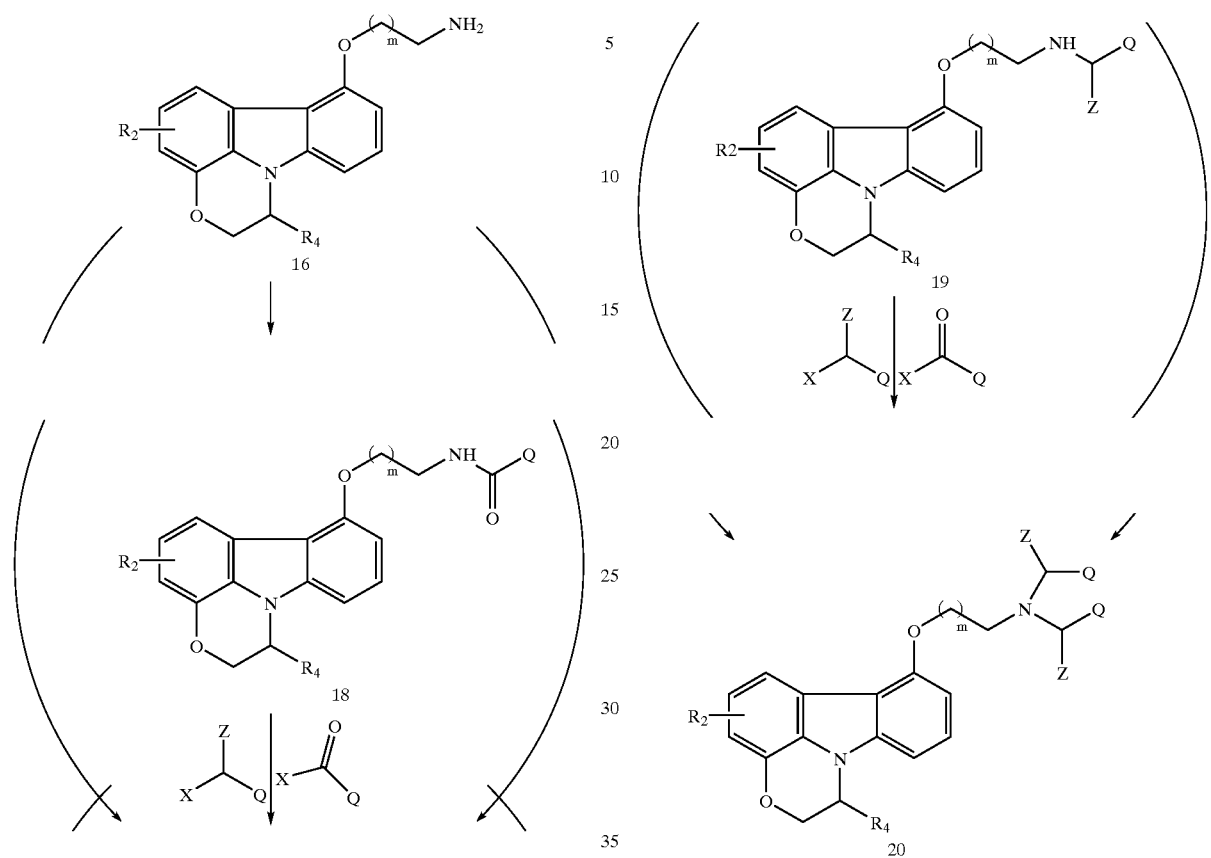
CHART D
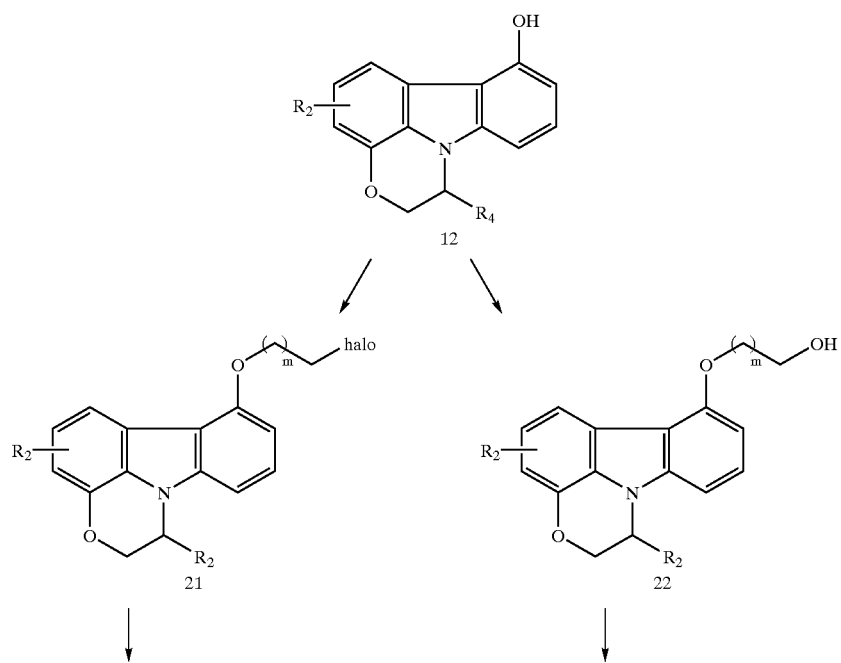

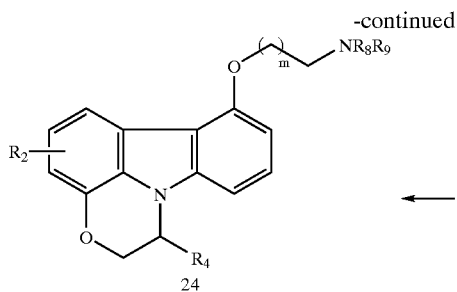
24

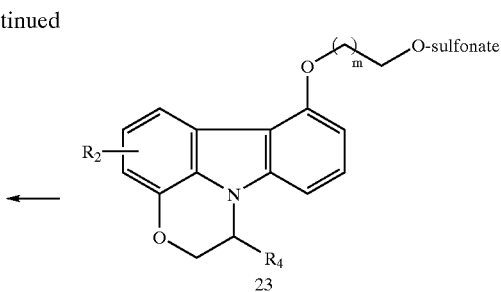
23

What is claimed is:

1. A method for treating a disease or condition in a mammal wherein the 5-HT receptor is implicated and modulation of 5-HT function is desired comprising administering a therapeutically effective amount of a compound of formula I to the mammal

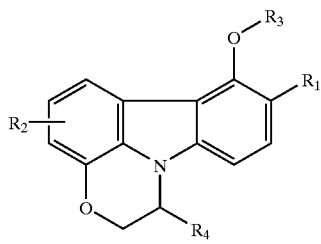
I or a pharmaceutically acceptable salt thereof wherein
$R_1$ is
   (a) H,
   (b) halo, or
   (c) $C_{1-6}$ alkyl;
$R_2$ is
   (a) H,
   (b) halo,
   (c) —OH,
   (d) —CN,
   (e) —CF$_3$,
   (f) —O($C_{1-6}$)alkyl,
   (g) $C_{1-6}$ alkyl,
   (h) $C_{3-6}$ cycloalkyl,
   (i) —NR$_5$R$_6$,
   (j) —CONR$_5$R$_6$,
   (k) —SO$_2$NR$_5$R$_6$,
   (l) —COOR$_7$, or
   (m) phenyl, optionally substituted with halo, OH, O($C_{1-4}$) alkyl, or $C_{1-6}$ alkyl;
$R_3$ is
   (a) —(CH$_2$)$_m$—NR$_8$R$_9$ wherein the —(CH$_2$)$_m$— chain may be substituted with one or two $C_{1-6}$ alkyl or $C_{3-6}$ cycloalkyl;
$R_4$ is
   (a) aryl, or
   (b) heteroaryl;
aryl is phenyl or naphthyl, optionally substituted with one or more $R_{10}$;
heteroaryl is a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein X is absent, H or $C_{1-4}$ alkyl; wherein carbon atoms of heteroaryl may be substituted with one or more $R_{10}$;
$R_5$ and $R_6$ is independently
   (a) H,
   (b) $C_{1-6}$ alkyl, or
   (c) $C_{3-6}$ cycloalkyl;
$R_7$ is
   (a) H,
   (b) $C_{1-6}$ alkyl, or
   (c) ($C_{1-3}$ alkyl)-phenyl [wherein phenyl may be substituted with $R_{10}$];
$R_8$ and $R_9$ is independently
   (a) H,
   (b) $C_{1-6}$ alkyl,
   (c) $C_{3-6}$ cycloalkyl,
   (d) $C_{2-4}$ alkyl substituted with —OH, —O($C_{1-4}$ alkyl), —O($C_{1-4}$ alkyl)-NR$_{11}$R$_{12}$, or —CO$_2$R$_5$,
   (e) —CHO, with the proviso that only one of the $R_8$ and $R_9$ is CHO, the other one is hydrogen,
   (f) —(CH$_2$)$_m$—phenyl wherein the phenyl may be substituted with halo, or
   (g) $R_8$ and $R_9$ taken together with the nitrogen to which they are attached form a five-,six-, or seven-membered heterocyclic ring wherein the heterocyclic ring optionally has one to two additional heteroatoms selected from the group consisting of oxygen, sulfur and N(Y) and wherein the carbon atoms of the heterocyclic ring is optionally substituted with one or two $R_{13}$; Y is absent or $R_{14}$;
$R_{10}$ is
   (a) halo,
   (b) —OH,
   (c) —CN,
   (d) —CF$_3$,
   (e) —O($C_{1-6}$)alkyl,
   (g) $C_{3-6}$ cycloalkyl,
   (h) —NR$_5$R$_6$,
   (i) —CONR$_5$R$_6$,
   (j) —SO$_2$NR$_5$R$_6$,
   (k) —COOR$_7$, or
   (l) phenyl, optionally substituted with halo, OH, O($C_{1-4}$) alkyl, or $C_{1-6}$ alkyl;
$R^{11}$ and $R_{12}$ is independently,
   (a) H, or
   (b) $C_{1-4}$ alkyl;
$R_{13}$ is
   (a) $C_{1-6}$ alkyl,
   (b) $C_{3-6}$ cycloalkyl,
   (c) $C_{2-4}$ alkyl substituted with —OH, —O($C_{1-4}$ alkyl), —O($C_{1-4}$ alkyl)—NR$_{10}$R$_{11}$, or —CO$_2$R$_5$,
   (d) —OH, or
   (e) oxo (=O);

$R_{14}$ is
  (a) H,
  (b) $C_{1-6}$ alkyl,
  (c) $C_{3-6}$ cycloalkyl,
  (d) $C_{2-4}$ alkyl substituted with —OH, —O($C_{1-4}$ alkyl), —O($C_{1-4}$ alkyl)—$NR_{10}R_{11}$, or —$CO_2R_5$,
  (e) —$COOR_7$,
  (f) —OH, or
  (g) oxo (=O); and m is 2, 3 or 4;
  wherein the compound is an antagonist of a 5-$HT_6$ receptor.

2. The method of claim 1, wherein the disease or condition is anxiety, depression, schizophrenia, a stress related disease, panic disorder, a phobia, obsessive compulsive disorder, post-traumatic-stress syndrome, immune system depression, psychosis, paraphrenia, mania, convulsive disorders, personality disorders, migraine headache, drug addiction, alcoholism, obesity, eating disorders, or sleep disorders.

3. The method of claim 1, wherein the disease or condition is psychotic, affective, vegetative, and psychomotor symptoms of schizophrenia and the extrapyramidal motor side effects of other antipsychotic drugs.

4. The method of claim 1 wherein the disease is anxiety, obesity, depression, or a stress related disease.

5. The method of claim 1 wherein the disease is obesity, depression, schizophrenia, schizophreniform disorder, schizoaffective disorder, delusional disorder, a stress related disease, panic disorder, a phobia, obsessive compulsive disorder, post-traumatic-stress syndrome, immune system depression, a stress induced problem with the urinary, gastrointestinal or cardiovascular system, neurodegenerative disorders, autism, chemotherapy-induced vomiting, hypertension, migraine headaches, cluster headaches, sexual dysfunction in a mammal, addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance, bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder, oppositional defiant disorder, peripheral neuropathy, post-traumatic stress disorder, premenstrual dysphoric disorder, a psychotic disorder, mood disorder, seasonal affective disorder, a sleep disorder, a specific developmental disorder, agitation disorder, or Tourette's syndrome.

6. A method for modulating 5-$HT_6$ receptor function, comprising contacting the receptor with an effective inhibitory amount of a compound as show in claim 1.

7. The method of claim 1 wherein said compound is administered rectally, topically, nasally, orally, sublingually, transderrnally or parenterally.

8. The method of claim 1 wherein said compound is administered in an amount from about 0.01 to about 150 mg/kg of body weight of said mammal per day.

9. The method of claim 1 wherein said compound is administered in an amount from about 0.1 to about 50 mg/kg of body weight of said mammal per day.

10. The method of claim 1 wherein said compound is administered in an amount from about 1 to about 30 mg/kg of body weight of said mammal per day.

11. The method of claim 1 wherein $R_1$ is H, $C_{1-4}$ alkyl or Cl.

12. The method of claim 1 wherein $R_1$ is H.

13. The method of claim 12 wherein $R_2$ is H or $CH_3$.

14. The method of claim 13 wherein $R_4$ is phenyl.

15. The method of claim 13 wherein $R_4$ is pyridyl, thiophene, benzothiophene, benzofuran, benzimidazole, imidazole or thiazole.

16. The method of claim 15 wherein $R_3$ is $(CH_2)_2$—$NR_8R_9$, wherein $R_8$ and $R_9$ are independently
  (a) H,
  (b) $C_{1-4}$ alkyl,
  (c) $C_{2-4}$ alkyl substituted with —OH,
  (i) (d) CHO, with the proviso that only one of the $R_8$ and $R_9$ is —CHO, the other one is hydrogen, or
  (e) $R_8$ and $R_9$ taken together with the nitrogen to which they are attached form
    (i) piperidine,
    (ii) pyrrolidine,
    (iii) morpholine,
    (iv) thiomorpholine, or
    (v) piperazine wherein one of the nitrogen is substituted with H, $C_{1-4}$ alkyl, or $CO_2(C_{1-4}$ alkyl).

17. The method of claim 15 wherein $R_3$ is —$(CH_2)_2$—$NR_8R_9$, wherein $R_8$ and $R_9$ are independently H, methyl, ethyl, ethanol, isopropyl, or $R_8$ and $R_9$ taken together with the nitrogen to which they are attached form 1-piperazinyl, 4-methyl-1-piperazinyl, 4-tert-butyl-1-piperazinecarboxylate, 4-morpholinyl, 1-piperidinyl, or 1-pyrrolidine.

18. The method of claim 15 wherein $R_3$ is —$(CH_2)_3$—$NR_8R_9$, wherein $R_8$ and $R_9$ are independently H, methyl, ethyl, ethanol, isopropyl, or $R_8$ and $R_9$ taken together with the nitrogen to which they are attached form 1-piperazinyl, 4-methyl-1-piperazinyl, 4-tert-butyl-1-piperazinecarboxylate, 4-morpholinyl, 1-piperidinyl, or 1-pyrrolidine.

19. The method of claim 15 wherein $R_3$ is —$(CH_2)_4$—$NR_8R_9$, wherein $R_8$ and $R_9$ are independently H, methyl, ethyl, ethanol, isopropyl, or $R_8$ and $R_9$ taken together with the nitrogen to which they are attached form 1-piperazinyl, 4-methyl-1-piperazinyl, 4-tert-butyl-1-piperazinecarboxylate, 4-morpholinyl, 1-piperidinyl, or 1-pyrrolidine.

20. The method of claim 1 wherein $R_1$ is Cl.

21. The method of claim 1 wherein $R_2$ is H, $C_{1-4}$ alkyl or halo.

22. The method of claim 1 wherein $R_2$ is H.

23. The method of claim 1 wherein $R_2$ is $CH_3$.

24. The method of claim 1 wherein $R_2$ is Cl or F.

25. The method of claim 1 wherein $R_3$ is $(CH_2)_2$—$NR_8R_9$, wherein $R_8$ and $R_9$ is independently
  (a) H,
  (b) $C_{1-4}$ alkyl,
  (c) $C_{2-4}$ alkyl substituted with —OH,
  (d) CHO, with the proviso that only one of the $R_8$ and $R_9$ is —CHO, the other one is hydrogen, or
  (e) $R_8$ and $R_9$ taken together with the nitrogen to which they are attached form
    (i) piperidine,
    (ii) pyrrolidine,
    (iii) morpholine,
    (iv) thiomorpholine, or
    (v) piperazine wherein one of the nitrogen is substituted with H, $C_{1-4}$ alkyl, or $CO_2(C_{1-4}$ alkyl).

26. The method of claim 1 wherein $R_3$ is —$(CH_2)_2$—$NR_8R_9$, wherein $R_8$ and $R_9$ is independently H, methyl, ethyl, ethanol, isopropyl, or $R_8$ and $R_9$ taken together with the nitrogen to which they are attached form 1-piperazinyl, 4-methyl-1-piperazinyl, 4-tert-butyl-1-piperazinecarboxylate, 4-morpholinyl,1-piperidinyl or 1-pyrrolidine.

27. The method of claim 1 wherein $R_4$ is phenyl.

28. The method of claim 1 wherein $R_4$ is pyridyl, thiophene, benzothiophene, benzofuran, benzimidazole, imidazole or thiazole.

29. The method of claim 1 wherein a compound of formula I is
   a) (S)-(+)-[(1-phenyl-1,2-dihydro[1,4]oxazino[2,3,4-jk]carbazol-7-yl)oxy]ethanamine,
   b) (R)-(−)-[(1-phenyl-1,2-dihydro[1,4]oxazino[2,3,4-jk]carbazol-7-yl)oxy]ethanamine,
   c) N,N-diethyl-2-[(1-phenyl-1,2-dihydro[1,4]oxazino[2,3,4-jk]carbazol-7-yl)oxy]-1-ethanamine,
   d) [(1-phenyl-1,2-dihydro[1,4]oxazino[2,3,4-jk]carbazol-7-yl)oxy]ethanamine,
   e) N-isopropyl-N-{2-[(1-phenyl-1,2-dihydro[1,4]oxazino[2,3,4-jk]carbazol-7-yl)oxy]ethyl}amine,
   f) N-ethyl-2-[(1-phenyl-1,2-dihydro[1,4]oxazino[2,3,4-jk]carbazol-7-yl)oxy]-1-ethanamine,
   g) 2-[(1-phenyl-1,2-dihydro[1,4]oxazino[2,3,4-jk]carbazol-7yl)oxy]ethylformamide,
   h) N-methyl-2-[(1-phenyl-1,2-dihydro[1,4]oxazino[2,3,4-jk]carbazol-7-yl)oxy]-1-ethanamine,
   i) 2-[(8-chloro-1-phenyl-1,2-dihydro[1,4]oxazino[2,3,4-jk]carbazol-7-yl)oxy]-1-ethanamine,
   j) 2-[(5-methyl-1-phenyl-1,2-dihydro[1,4]oxazino[2,3,4-jk]carbazol-7-yl)oxy]-1-ethanamine,
   k) N-ethyl-2-[(5-methyl-1-phenyl-1,2-dihydro[1,4]oxazino[2,3,4-jk]carbazol-7-yl)oxy]-1-ethanamine,
   l) tert-butyl 4-{2-[(1-phenyl-1,2-dihydro[1,4]oxazino[2,3,4-jk]carbazol-7-yl)oxy]ethyl}-1-piperazinecarboxylate,
   m) 1-phenyl-1,2-dihydro[1,4]oxazino[2,3,4-jk]carbazol-7-yl 2-(1-piperazinyl)ethyl ether,
   n) 2-(4-methyl-1-piperazinyl)ethyl 1-phenyl-1,2-dihydro[1,4]oxazino[2,3,4-jk]carbazol-7-yl ether,
   o) 2-(4-morpholinyl)ethyl 1-phenyl-1,2-dihydro[1,4]oxazino[2,3,4-jk]carbazol-7yl ether,
   p) 1-phenyl-1,2-dihydro[1,4]oxazino[2,3,4-jk]carbazol-7-yl 2-(1-piperidinyl)ethyl ether,
   q) 2-({2-[(1-phenyl-1,2-dihydro[1,4]oxazino[2,3,4-jk]carbazol-7-yl)oxy]ethyl}amino)-1-ethanol,
   r) N,N-dimethyl-2-[(1-phenyl-1,2-dihydro[1,4]oxazino[2,3,4-jk]carbazol-7-yl)oxy]-1-ethanamine,
   (s) 2-[(5-Methyl-1-phenyl-1,2-dihydro[1,4]oxazino[2,3,4-jk]carbazol-7-yl)oxy]-1-ethanamine,
   (t) N,N-Diethyl-N-{4-[(1-phenyl-1,2-dihydro[1,4]oxazino[2,3,4-jk]carbazol-7-yl)oxy]butyl}-amine,
   (u) N,N-Diethyl-N-{3-[(1-phenyl-1,2-dihydro[1,4]oxazino[2,3,4-jk]carbazol-7-yl)oxy]propyl}amine,
   (v) [(2-{[(1R)-1-Phenyl-1,2-dihydro[1,4]oxazino[2,3,4-jk]carbazol-7-yl]oxy}ethyl)amino]ethanol, or pharmaceutically acceptable salt thereof.

* * * * *

UNITED STATES PATENT AND TRADEMARK OFFICE
CERTIFICATE OF CORRECTION

PATENT NO.   : 6,821,970 B2
DATED        : November 23, 2004
INVENTOR(S)  : Ruth Elizabeth TenBrink et al.

It is certified that error appears in the above-identified patent and that said Letters Patent is hereby corrected as shown below:

Title page,
Item [56], References Cited, OTHER PUBLICATIONS,
delete "Boess et al. Mol. Pharmacol. 1998, 54, 577-583"
delete "Monsma et al. M I. Pharmacol. 1993, 43, 320-327"

Column 45,
Line 44, "(t) -O($C_{1-6}$)alkyl," should read -- (f) -O($C_{1-6}$)alkyl, --

Column 46,
Line 50, "(e) -O($C_{1-6}$)alkyl," insert next line, -- (f) $C_{1-6}$ alkyl, --

Column 47,
Line 55, "transderrnally or parenterally" should read -- transdermally or parenterally --

Column 49,
Line 25, "carbazol-7yl)oxy]ethylformamide," should read
-- carbazol-7-yl)oxy]ethylformamide, --

Column 50,
Line 13, "oxazino[2,3,4-jk]carbazol-7yl ether," should read
-- oxazino[2,3,4-jk]carbazol-7-yl ether, --

Signed and Sealed this

Twenty-fourth Day of May, 2005

JON W. DUDAS
*Director of the United States Patent and Trademark Office*